US008017571B2

(12) United States Patent
Rougeot et al.

(10) Patent No.: US 8,017,571 B2
(45) Date of Patent: Sep. 13, 2011

(54) PEPTIDES DERIVED FROM HUMAN BPLP PROTEIN

(75) Inventors: Catherine Rougeot, Chevreuse (FR); Jean-Francois Huaulme, Paris (FR); Marie-Noelle Ungeheuer, Maurepas (FR); Anne Wisner, Cachan (FR); Evelyne Dufour, Vanves (FR)

(73) Assignee: Institut Pasteur, Paris (FR)

( * ) Notice: Subject to any disclaimer, the term of this patent is extended or adjusted under 35 U.S.C. 154(b) by 551 days.

(21) Appl. No.: 10/593,071

(22) PCT Filed: Mar. 18, 2005

(86) PCT No.: PCT/IB2005/000700
§ 371 (c)(1),
(2), (4) Date: Jan. 19, 2007

(87) PCT Pub. No.: WO2005/090386
PCT Pub. Date: Sep. 29, 2005

(65) Prior Publication Data
US 2008/0206230 A1    Aug. 28, 2008

(30) Foreign Application Priority Data

Mar. 19, 2004  (EP) .................................... 04290754

(51) Int. Cl.
A61K 38/04           (2006.01)
(52) U.S. Cl. ........................................ 514/1.1; 530/300
(58) Field of Classification Search .................... None
See application file for complete search history.

(56) References Cited

U.S. PATENT DOCUMENTS

| | | | |
|---|---|---|---|
| 5,859,189 A | 1/1999 | Rosinski-Chupin et al. |
| 6,025,143 A | 2/2000 | Rosinski-Chupin et al. |
| 6,589,750 B2 | 7/2003 | Rougeot et al. |
| 6,818,405 B2 | 11/2004 | Rougeot et al. |
| 6,916,607 B2 | 7/2005 | Rosinski-Chupin et al. |
| 7,153,833 B2 | 12/2006 | Rougeot et al. |
| 7,387,778 B2 | 6/2008 | Marcel et al. |
| 7,423,020 B2 | 9/2008 | Rougeot et al. |
| 7,429,448 B2 | 9/2008 | Rougeot et al. |
| 7,625,713 B2 | 12/2009 | Rougeot et al. |
| 2003/0186870 A1 | 10/2003 | Marcel et al. |
| 2003/0195155 A1 | 10/2003 | Rougeot et al. |
| 2005/0153374 A1 | 7/2005 | Rosinski-Chupin et al. |
| 2008/0206230 A1 | 8/2008 | Rougeot et al. |
| 2009/0253639 A1 | 10/2009 | Rougeot et al. |
| 2009/0298109 A1 | 12/2009 | Rougeot et al. |
| 2010/0041072 A1 | 2/2010 | Rougeot et al. |

FOREIGN PATENT DOCUMENTS

| | | |
|---|---|---|
| EP | 1 216 707 | 6/2002 |
| EP | 1 577 320 | 9/2005 |
| WO | 98 37100 | 8/1998 |
| WO | 2009 090265 | 7/2009 |
| WO | 2009 124948 | 10/2009 |
| WO | 2009 150040 | 12/2009 |
| WO | 2010 060995 | 6/2010 |

OTHER PUBLICATIONS

Duckert et al. Prediction of proprotein convertase cleavage sites. Protein Engineering, Design and Selection, 2004, 17(1): 107-112.*
Dickinson Douglas P. et al., "CDNA Cloning of an Abundant Human Lacrimal Gland MRNA Encoding A Novel Tear Protein", Current Eye Research, vol. 15, XP 009035462, pp. 377-386, 1996.
Firla Beate et al., "Extracellular Cysteines Define Ectopeptidase (APN, CD13) Expression and Function", Free Radical Biology and Medicine, vol. 32, XP 002293336. pp. 584-595, 2002.
Wisner, A. et al., "Human Opiorphin, A Natural Antinociceptive Modulator Of Opioid-Dependent Pathways", Proceedings of the National Academy of Sciences of USA, vol. 103, No. 47. pp. 17979-17984, XP002499569, ISSN: 0027-8424, (Nov. 21, 2006).
International Search Report issued Mar. 1, 2010 in PCT/EP09/056390 filed May 26, 2009.
U.S. Appl. No. 12/994,534, filed Nov. 24, 2010, Rougeot.
U.S. Appl. No. 07/499,276, filed Jul. 19, 1990, Rosinski-Chupin, et al.
U.S. Appl. No. 09/599,927, filed Jun. 22, 200, Marcel, et al.
U.S. Appl. No. 12/580,701, filed Oct. 15, 2009, Rougeot et al.
U.S. Appl. No. 10/593,071, filed Jan. 19, 2007, Rougeot et al.
U.S. Appl. No. 12/357,192, filed Jan. 21, 2009, Rougeot.
U.S. Appl. No. 12/936,591, filed Dec. 22, 2010, Rougeot.

* cited by examiner

*Primary Examiner* — Dong Jiang
(74) *Attorney, Agent, or Firm* — Oblon, Spivak, McClelland, Maier & Neustadt, L.L.P.

(57) ABSTRACT

The invention relates to a peptide that is a maturation product of the Basic Prolin-rich Lacrinal Protein (BPLP) or a peptide derivative of said maturation product, wherein the peptide or peptide derivative exhibits an inhibitory property against a metallo-ectopeptidase, especially NEP and/or APN.
The present invention also relates to polynucleotides coding for said peptides and to antibodies directed against said peptides. Furthermore, the present invention relates to diagnostic and therapeutic uses of human BPLP protein and inhibitory peptides derived therefrom, polypeptides coding for human BPLP protein or peptides derived therefrom as well as antibodies directed against BPLP protein or peptides derived therefrom.

9 Claims, 12 Drawing Sheets

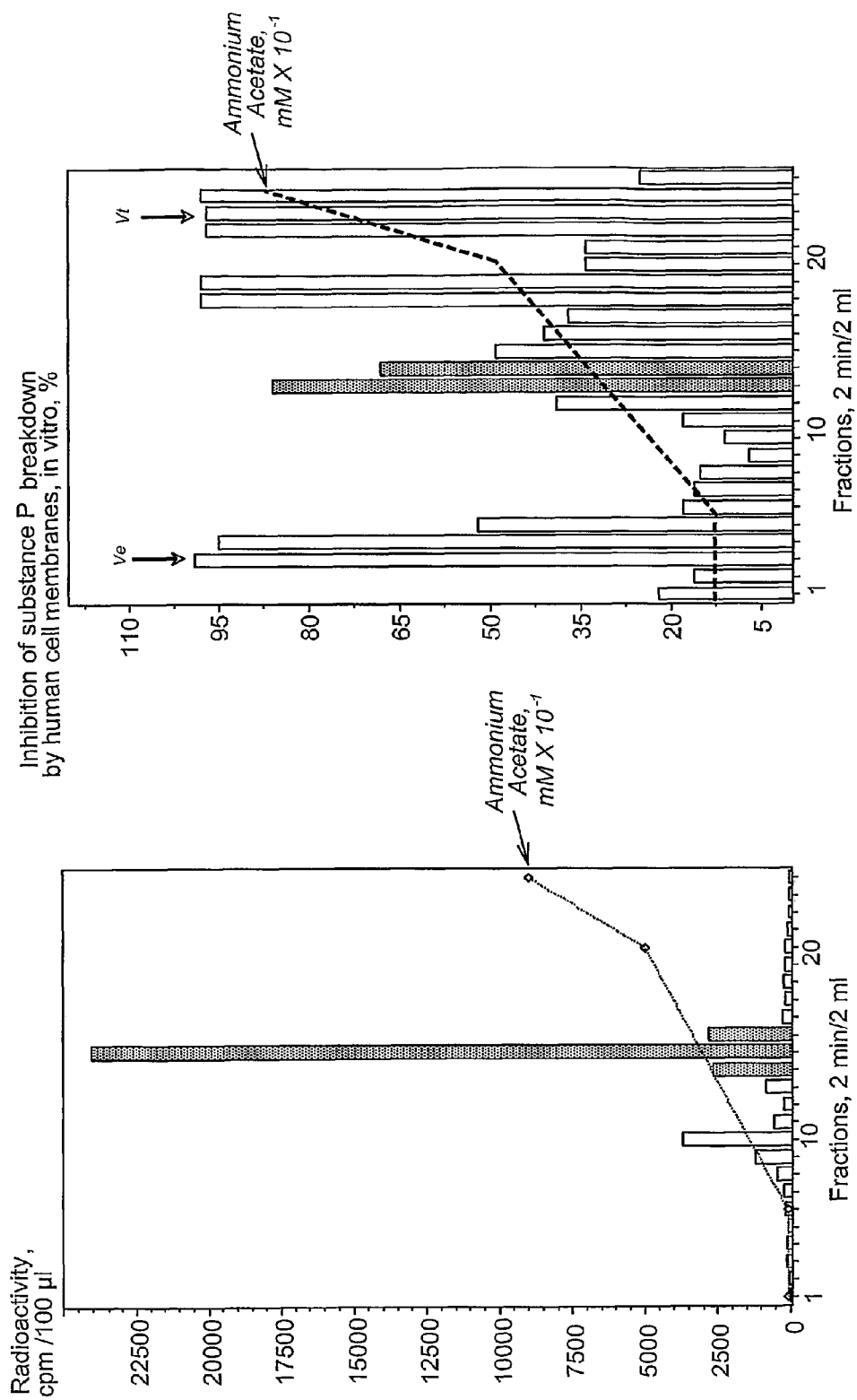

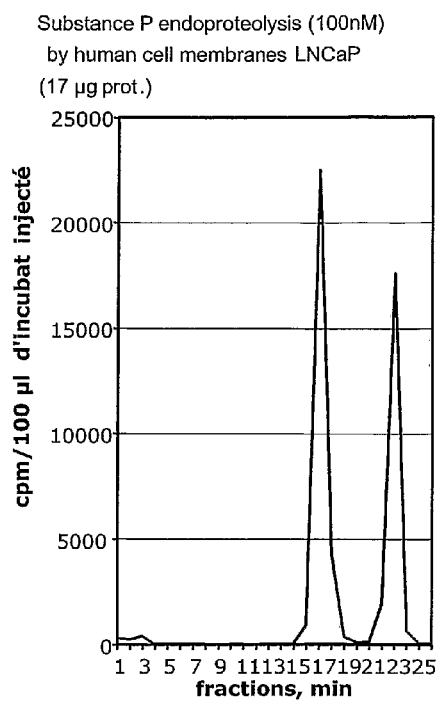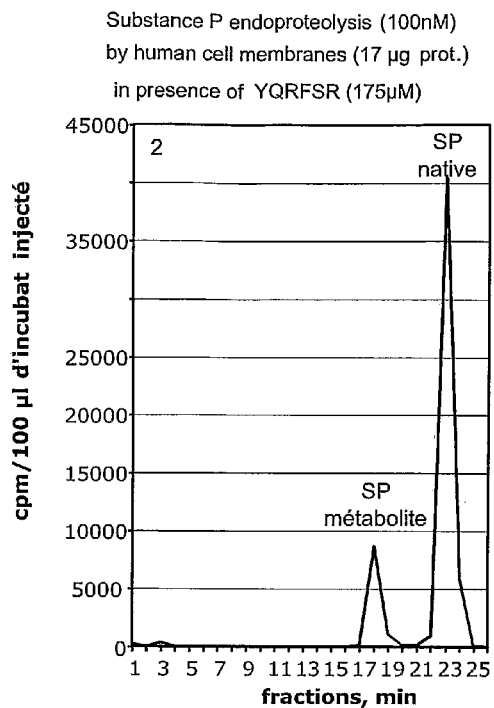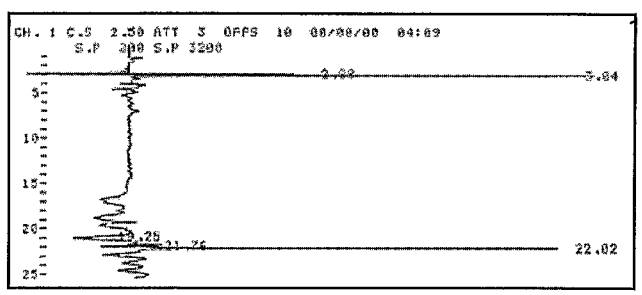
FIG.8

PEPTIDES DERIVED FROM HUMAN BPLP PROTEIN

CROSS-REFERENCE TO RELATED APPLICATIONS

The present application is a 35 U.S.C. §371 National Stage patent application of International patent application PCT/IB05/000700, filed on Mar. 18, 2005, which claims priority to European patent application EP 04290754.3, filed on Mar. 19, 2004.

The present invention relates to peptides derived from human BPLP protein, as new inhibitors of metallo-ectopeptidases. The present invention also relates to polynucleotides coding for said peptides and to antibodies directed against said peptides. Furthermore, the present invention relates to diagnostic and therapeutic uses of human BPLP protein, peptides derived therefrom and mimetics thereof, polypeptides coding for human BPLP protein or peptides derived therefrom as well as antibodies directed against BPLP protein or peptides derived therefrom.

In a genomic approach, an androgen-regulated gene, which is predominantly expressed in the submandibular gland (SMG) and prostate of adult rats, has been identified (Rosinski-Chupin et al., 1988 and European patent 0 394 424). The gene encodes a precursor protein, submandibular rat$_1$ protein (SMR$_1$) giving rise to three structurally related peptides which are selectively matured from the precursor in vivo by cleavage at multibasic sites by a paired basic amino acid-converting enzyme (Rougeot et al., 1994).

In an approach of post-genomic and physiomic, it was established the molecular and functional bases providing evidence for the existence in mammals of a hormonal messenger of the intercellular communication, i.e., the final mature peptide generated from SMR1 pre-prohormone: SMR1-Pentapeptide, named today Sialorphin (of sequence QHNPR (SEQ ID NO: 8)). Hence, sialorphin is an exocrine and endocrine peptide-signal, whose expression is under activational androgenic regulation and secretion is evoked under adrenergic-mediated response to environmental stress, in male rat (Rougeot et al., 1997).

The fact that, in sexually mature male rat, the androgen-regulated sialorphin is acutely secreted in response to environmental acute stress, led to postulate that this signaling mediator might play a role in some physiological and behavioral integration linked to the reproduction. Thus the same authors investigated the effects induced by sialorphin on the male sexual behavior pattern, which included frequency and latency of mounts, intromissions and ejaculations, as well as socio-sexual interactions. The data obtained showed that sialorphin has the ability to modulate, at doses related to physiological circulating levels, the male rat mating pattern, i.e., exerting, in a dose-dependent manner, a dual facilitative/inhibitory effect on the sexual performance, while stimulating at all doses the apparent sexual arousal or motivation. Thus it is proposed that the endogenous androgen-regulated sialorphin helps modulate the adaptative balance between excitatory and inhibitory mechanisms serving appropriate male rat sexual response, depending on the context.

International patent application WO 01/00221 describes the use of maturation products of SMR1 for the treatment of impaired interpersonal and behavioural disorders, including sexual defects.

Furthermore, these authors discovered that SMR1 maturation products recognize specific target sites in organs that are deeply involved in the mineral ion concentration. International patent application WO 98/37100 describes the therapeutic use of maturation products of SMR1 for preventing or treating diseases associated with a mineral ion imbalance in a human or an animal body.

In response to stressful contexts, sialorphin is acutely released, rapidly distributed and lasting taken up by its systemic membrane-associated targets (Rougeot et al., 1997). The authors have demonstrated that the major cell surface molecule to which sialorphin binds in vivo is the membrane-anchored metalloecto-endopeptidase, NEP (Neutral Endopeptidase; Neprilysin EC 3.4.24.11), or enkephalinase (Rougeot et al., 2003). Moreover, sialorphin was shown to be a physiological antagonist of the NEP activity ex vivo; and the direct interaction of NEP and sialorphin assessed in an in vitro assay using soluble purified renal NEP and artificial fluorogenic DGNPA (Dansyl-Gly-(pNO2)Phe-βAla) as substrate provided direct evidence that sialorphin inhibited NEP activity (IC 50 of the sialorphin: 0.6 µM). Sialorphin, is the first physiological inhibitor of the NEP-enkephalinase activity identified to date in rodent (Rougeot et al., 2003 and European patent application EP 1 216 707).

NEP is located at the surface of cells in nervous and systemic tissues, where it plays an important function as an ectoenzyme catalyzing the post-secretory processing or metabolism of a number of neuropeptides and regulatory peptides. The main physiologically relevant substrates for NEP are the enkephalins, substance P and atrial natriuretic peptide (ANP). These mammalian signal peptides are involved in the control of central and peripheral pain perception, inflammatory phenomena, arterial tone and mineral homeostasis. Their physiological importance and the critical role of NEP ectoenzyme in modulating their functional potency make it important to investigate and know their possible protection by endogenous inhibitors, from a physiological as well as a physiopathological and therapeutic point of view.

By using different models of molecular and behavioral pharmacology, the authors have shown that the physiological mediator, sialorphin, prevents spinal and renal NEP from breaking down its two physiologically relevant substrates, Substance P and Met-enkephalin in vitro. Sialorphin inhibited the breakdown of substance P with an IC50 of 0.4-1 µM and behaved as a competitive inhibitor of the membrane-bound NEP that originates from nervous tissues (spinal cord) or from systemically tissues (kidney, bone, tooth, placenta, prostate, GSM, intestine). In vivo, intravenous sialorphin elicited potent antinociceptive responses in two behavioral rat models of injury-induced acute and tonic pain, the pin-pain test (mechanical algesia) and formalin test (chemical algesia). The analgesia induced by sialorphin required the activation of µ- and δ-opioid receptors, consistent with the involvement of endogenous opioid receptors in enkephalinergic transmission. Indeed, these receptors are involved in the transmission of the endogenous opioidergic signals such as the enkephalins which are inactivated by NEP and the aminopeptidase APN, and also of the exogenous opiate, the morphine which interacts mainly with the µ-opioid receptor. It was concluded that the sialorphin protects endogenous enkephalins released following nociceptive stimuli by inhibiting ecto-enkephalinases, in vivo, and thus potentialises their analgesic effect. Otherwise, the endogenous opioid system, in particular δ-opioid-mediated pathway, has also been linked to the etiology of depressive behavior; for instance using a model of analysis of behavioral despair (forced swim test), the authors showed that sialorphin displays a significative antidepressant activity in male rat. Sialorphin is the first natural systemically active regulator of NEP activity identified to date in mammals. Furthermore, evidence was provided that it is a new physiological modulator of pain perception following injury, and may be the progenitor of a new class of therapeutic molecules, as putative novel antinociceptive and antidepressive agents (Rougeot et al., 2003; EP 1,343,519 and EP 1,343,520).

The powerful analgesic effect of sialorphin is associated to its capacity to entirely protect the enkephalins from inactivation by the enkephalin-degrading ectoenzymes. In vivo, the enkephalins are inactivated with an extraordinarily efficiency (within few seconds) by the both ectopeptidases, NEP and APN. In agreement, the first developed synthetic inhibitors, which are either only NEP specific (such as Thiorphan) or APN specific (such as Bestatin) exhibit a non-significant or weak antinociceptive effect. Thus, rat sialorphin is a physiological dual inhibitor of NEP and APN metallo-ectopeptidases; furthermore, this endocrine signal messenger of the adaptative response to stress is a powerful inhibitor of painful perception in rat and its analgesic effect is more potent than that of synthetic dual NEP/APN inhibitors such as kelatorphan, which have been developed elsewhere by modeling methods. So, sialorphin is remarkably adapted in terms of specificity and bioavailability to the conformational and distributive characteristics of its targets and as a consequence is more effective from an integrative point of view. Considering these observations, from a functional as well as physiopathological and therapeutic point of view, the biological importance of the functions regulated by the rat sialorphin makes it crucial to investigate and identify the endogenous functional homologous of rat sialorphin in human.

Sialorphin is the only identified physiological systemically active regulator of the membrane-bound enkephalinase activity in mammals. This raises the question of the existence of such endogenous NEP-ectopeptidase inhibitor in human saliva and blood. No immunoreactive QHNPR peptide (SEQ ID NO: 8) (sialorphin) was detected in male human saliva using highly sensitive and specific radioimmunoassay (Rougeot et al., 1994). However, bibliographical data let suppose the presence of low molecular weight substances ($\leq 3000$ Da), inhibiting the NEP ectopeptidase activity in human, notably in the human saliva. Although this(ese) salivary component(s) was(were) not biochemically characterized, a gender-related difference was observed in the salivary production of this(ese) inhibitor(s) of human enkephalin-degrading ectoenzymes (Marini and Roda, 2000). Strikingly, the situation is very similar to that one identified by the inventors in male rat, wherein the submandibular gland and the saliva represented the compartments of major synthesis and secretion of sialorphin, respectively.

The gene encoding the SMR1 precursor of sialorphin belongs to a multigene family whose members have been identified in human. However, the stricto sensu homologous human gene of rat SMR1 gene (VCSA1 coding for SMR1) was not found in human (cDNA cloning and human genome analysis). Furthermore, the inhibitory potency of rat sialorphin against membrane-anchored human NEP, which is expressed by human prostate cell lines (LNCaP), exists but is about 10-fold lower than that obtained against rodent NEP (rat, rabbit). This apparent selectivity in the functional interaction between rat sialorphin and NEP ectoenzyme is at least surprising considering the fact that the rat and human NEP have relatively high amino-acid sequence analogy (about 85%). Otherwise, the characterization of the human genes of the multigenic family to which belongs the gene coding for the precursor of the rat sialorphin (SMR1), revealed that it exists in human, several genes of this family, among which three were characterized, i.e., the genes hPB, hPBI and BPLP which are clustered in the same chromosome region, q13-21 of Chromosome 4 (Isemura, 2000) (Isemura and Saitoh, 1997) (Dickinson and Thiesse, 1996).

The inventors have now identified a new peptide that is considered as the functional human homologous of the SMR1-pentapeptide sialorphin.

The numerous data collected by the inventors support that the new peptide, of sequence QRFSR (SEQ ID NO: 3), derives from the BPLP protein ("Basic Proline-rich Lacrimal Protein").

The human gene BPLP codes for a polypeptide sequence of 201 amino-acids (with the potential signal peptide of secretion) predicted from the cDNA cloned and characterized by Dickinson and al. (Dickinson and Thiesse, 1996). The gene BPLP is expressed in human lacrimal and submandibular glands. In the annexed sequence listing, SEQ ID No. 1 shows the cDNA sequence coding for BPLP, and SEQ ID No. 2 shows the BPLP aminoacid sequence.

The inventors defined consensus sites in the best conserved N-terminal region (between the rat, mouse and human) of the secreted BPLP protein, on the basis of the maturation processing of rat sialorphin from the SMR1 precursor.

For instance, these consensus sites were defined as signal peptide cleavage sites in a region having the sequence required for the signal peptidase and at paired basic residues with R—R bonds recognized as processing signal for paired basic amino acid-convertase.

At such consensus sites, the inventors then found out a sequence QRFSR (SEQ ID NO: 1), structurally closely related to that of rat QHNPR sialorphin (SEQ ID NO: 8).

This peptide was synthesized and analyzed for its capacity to inhibit the degradation of the physiological NEP substrate, i.e. substance P.

This peptide was then identified as the human functional homologous of sialorphin.

The present invention is drawn to peptides derived from human BPLP protein, as new inhibitors of metallo-ectopeptidases.

More particularly, the present invention is drawn to maturation products of the BPLP protein, in particular the QRFSR peptide (SEQ ID NO: 3), as well as peptide derivatives and mimetics thereof, useful to potentialise the effects of neuroendocrine peptide messengers which control the nociceptive transmission (e.g. enkephalins), the well-being and/or the homeostatic exchanges of Na/Pi/Ca/H2O mainly (e.g. natriuretic peptides).

The present invention is also drawn to polynucleotides coding for said peptides and peptide derivatives as well as to antibodies directed against said peptides and peptide derivatives thereof.

Furthermore, the present invention is drawn to diagnostic and therapeutic uses of human BPLP protein, human BPLP protein-derived peptides, and peptides derivatives and mimetics thereof, as well as diagnostic and therapeutic uses of polynucleotides coding for human BPLP protein, human BPLP protein-derived peptides and peptides derivatives thereof and of antibodies directed against human BPLP protein, human BPLP protein-derived peptides and peptide derivative thereof.

It should be understood that the peptides, proteins, or nucleic acids of the invention are in isolated or purified form.

By <<purified>> and <<isolated>> it is meant, when referring to a protein or peptide (including antibodies) or a nucleotide sequence, that the indicated molecule is present in the substantial absence of other biological molecules. The term "purified" as used herein preferably means at least 75% by weight, more preferably at least 85% by weight, more preferably still at least 95% by weight, and most preferably at least 98% by weight, of biological molecules of the same type are present. An "isolated" or "purified" nucleic acid molecule which encodes a particular polypeptide refers to a nucleic acid molecule which is substantially free of other nucleic acid molecules that do not encode the subject polypeptide. However, the molecule may include some additional bases or moieties which do not deleteriously affect the basic characteristics of the composition.

Peptides

For purposes of the invention, a "peptide" is a molecule comprised of a linear array of amino acid residues connected to each other in the linear array by peptide bonds. Such linear array may optionally be cyclic, i.e., the ends of the linear peptide or the side chains of amino acids within the peptide may be joined, e.g., by a chemical bond. Such peptides according to the invention may include from about three to about 500 amino acids, preferably from about 3 to about 100 amino acids, and most preferably from about 3 to about 50 amino acids and especially from about 3 to 15 amino acids and may further include secondary, tertiary or quaternary structures, as well as intermolecular associations with other peptides or other non-peptide molecules. Such intermolecular associations may be through, without limitation, covalent bonding (e.g., through disulfide linkages), or through chelation, electrostatic interactions, hydrophobic interactions, hydrogen bonding, ion-dipole interactions, dipole-dipole interactions, or any combination of the above.

In these peptides, by N-terminal cyclization/decyclization, Glp and Gln interconvert.

A subject of the present invention is a peptide which is derived from human BPLP protein and which has a modulatory, especially an inhibitory activity on metallo-ectopeptidases.

"Derived from human BPLP protein" means which comprises, consists essentially of, or consists of a BPLP protein fragment. In a preferred embodiment, said peptide consists of 3 to about 150 amino acids. Most preferably, said peptide consists of less than 100 amino acids.

Particularly a subject of the present invention is a maturation product of the BPLP protein as well as peptide derivatives thereof.

More particularly, it is drawn to a peptide that is a maturation product of the Basic Proline-rich Lacrinal Protein (BPLP) or peptide derivative of said maturation product, wherein the peptide or peptide derivatives exhibits an inhibitory property against a metallo-ectopeptidase, especially NEP and/or APN, and more particularly NEP.

A "maturation product" is a peptide that is obtained through cleavage of the BPLP protein precursor by natural maturases or prohormone converting enzymes, or related mono or paired basic amino acid-cleaving enzymes such as furin, PC convertases or PACE 4 (Seidah, 1995), for example.

The peptides of the invention include "peptide derivatives".

The "peptides derivatives" are peptides having amino acid substitutions from a parent peptide, preferably from one to two amino acid substitutions from a parent peptide particularly when said parent peptide comprises less than 15 amino acids and preferably less than 10 amino acids, but retaining the binding specificity and/or physiological activity of the parent peptide. As used herein, "retaining the binding specificity of the parent peptide" means being able to bind to a monoclonal or polyclonal antibody that binds to one of the BPLP maturation products or to the BPLP maturation product receptor with an affinity that is at least one-tenth, more preferably at least one-half, and most preferably at least as great as that of one of the peptides that are maturation products of BPLP. Determination of such affinity is preferably conducted under standard competitive binding immunoassay conditions. "Retaining the physiological activity of the parent peptide" means retaining the ability of any one of the BPLP maturation peptides to bind and to modulate the activity of a metallo-ectopeptidase, especially NEP and/or APN, and more particularly NEP, and so to optimize the local and systemic nociceptive, inflammatory, anti-depressant, and/or ion homeostatic responses to stress. Determining whether such activity is modulated is further described later in this specification.

The peptides of the invention include peptides or peptide derivatives which comprise, consist essentially of or consist of sequence X1-X2-Arg-Phe-Ser-Arg (SEQ ID NO: 6), wherein X1 represents H, Tyr, or Cys, X2 represents Gln or Glp when X1 is H, or X2 represents Gln when X1 is Tyr or Cys. When the peptide of the invention comprises or consists essentially of sequence X1-X2-Arg-Phe-Ser-Arg (SEQ ID NO: 6), said sequence is the C-terminal part of the peptide of the invention.

Preferred peptides according to the invention comprise, consist essentially of, or consist of sequence QRFSR (SEQ ID NO: 3).

More particularly a peptide of the invention is the peptide that consists of sequence QRFSR (SEQ ID No. 3).

Another peptide of the invention is the peptide that consists of sequence YQRFSR (SEQ ID No. 4).

Still another peptide of the invention is the peptide that consists of sequence CQRFSR (SEQ ID NO: 5).

Yet another peptide of the invention is the peptide that consists of sequence GlpRFSR (SEQ ID NO: 7).

Throughout the text,
Glp is pyroglutamate,
Tyr or Y is Tyrosine,
Gln or Q is glutamine,
Arg or R is Arginine,
Phe or F is Phenylalanine,
Ser or S is Serine,
Cys or C for Cystine.

The peptides according to the present invention may be prepared in a conventional manner by peptide synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis the technique described by Merrifield may be used in particular. Alternatively, the technique described by Houbenweyl in 1974 may also be used.

For more details, reference may be made to WO 98/37100.

The peptides according to the present invention may also be obtained using genetic engineering methods.

Preferred mimetics, including peptidomimetics, retain the binding specificity and/or physiological activity of the parent peptide including peptide derivative, as described above. As used herein, a "mimetic" is a molecule that mimics some properties of the natural peptides, preferably their binding specificity and physiological activity. Preferred mimetics are obtained by structural modification of peptides according to the invention, preferably using unnatural amino acids, D aminoacid instead of L aminoacid, conformational restraints, isosteric replacement, cyclization, or other modifications. Other preferred modifications include without limitation, those in which one or more amide bond is replaced by a non-amide bond, and/or one or more amino acid side chain is replaced by a different chemical moiety, or one or more of the N-terminus, the C-terminus or one or more side chain is protected by a protecting group, and/or double bonds and/or cyclization and/or stereospecificity is introduced into the amino acid chain to increase rigidity and/or binding affinity.

Based on the crystal structure of the binding domain of the metallo-ectopeptidase targeted by the peptide of the invention, mimetics can also be obtained by means of computer-assisted drug design development (Oefner et al. (2000); Gomeni et al. (2001); Jones et al. (2002); Kan (2002)).

Still other preferred modifications include those intended to enhance resistance to enzymatic degradation, improvement in the bioavailability in particular by nervous and gonad tissues and more generally in the pharmacokinetic properties and especially comprise:

protecting the $NH_2$ and COOH hydrophilic groups by esterification (COOH) with lipophilic alcohols or by amidation (COOH) and/or by acetylation ($NH_2$) or added carboxyalkyl or aromatic hydrophobic chain at the $NH_2$ terminus;

retroinversion isomers of the CO—NH amide bonds or methylation (or ketomethylene, methyleneoxy, hydroxyethylene) of the amide functions;

substitution of L aminoacids for D aminoacids.

All of these variations are well known in the art. Thus, given the peptide sequences disclosed herein, those skilled in the art are enabled to design and produce mimetics having binding characteristics and/or physiological activities similar to or superior to such peptides (see e.g., Horwell et al., (1996); Liskamp et al., (1994); Gante et al., (1994); Seebach et al., (1996)).

As used herein, the term "BPLP-peptide" refers to BPLP protein, peptides derived from BPLP, BPLP maturation peptides, and peptides derivatives and mimetics, including peptidomimetics, of the invention.

The invention also relates to a molecular complex comprising:

a metallo-ectopeptidase receptor, especially a NEP receptor or an APN receptor, especially a NEP receptor, binding site of the BPLP-protein or maturation products thereof, e.g. QRFSR (SEQ ID NO: 3);

the BPLP-protein or maturation products thereof, e.g. QRFSR (SEQ ID NO: 3).

Nucleic Acids, Methods of Expression and Methods of Detection

The nucleic acids, also named polynucleotides, such as DNA or RNA molecules, that encode the peptides, including peptides derivatives, defined above are also part of the invention, while taking into account the degeneration of the genetic code.

Accordingly, the present invention provides nucleic acids coding for peptides derived from human BPLP protein, and peptides derivatives thereof.

Particularly, the present invention provides nucleic acids coding for peptides which comprise, consist essentially of, or consist of sequence X1-X2-Arg-Phe-Ser-Arg (SEQ ID NO: 6) as above defined. When the peptide of the invention comprises or consists essentially of sequence X1-X2-Arg-Phe-Ser-Arg (SEQ ID NO: 6), said sequence is the C-terminal part of the peptide of the invention. In preferred embodiments, the present invention provides acid nucleic coding for peptides which comprise, consist essentially of, or consist of sequence QRFSR (SEQ ID NO: 3). In a most preferred embodiment, the present invention provides a nucleic acid coding for QRFSR (SEQ ID NO: 3) or a nucleic acid coding for YQRFSR (SEQ ID NO: 4).

The nucleic acids of the invention include sequences that are hybridizable to any of the above sequences or their complementary sequences under standard hybridization conditions, preferably conditions of high stringency.

A nucleic acid molecule is "hybridizable" to another nucleic acid molecule, when a single stranded form of the nucleic acid molecule can anneal to the other nucleic acid molecule under the appropriate conditions of temperature and solution ionic strength (see Sambrook et al., 1989). The conditions of temperature and ionic strength determine the "stringency" of the hybridization. For preliminary screening for homologous nucleic acids, low stringency hybridization conditions, corresponding to a Tm (melting temperature) of 55° C., can be used, e.g., 5×SSC, 0.1% SDS, 0.25% milk, and no formamide; or 30% formamide, 5×SSC, 0.5% SDS). Moderate stringency hybridization conditions correspond to a higher Tm, e.g., 40% formamide, with 5× or 6×SCC. High stringency hybridization conditions correspond to the highest Tm, e.g., 50% formamide, 5× or 6×SCC. SCC is a 0.15 M NaCl, 0.015 M Na-citrate. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridization with shorter nucleic acids, i.e., oligonucleotides, the position of mismatches becomes more important, and the length of the oligonucleotide determines its specificity (see Sambrook et al., supra, 11.7-11.8). A minimum length for a hybridizable nucleic acid is at least about 10 nucleotides; preferably at least about 15 nucleotides.

In a specific embodiment, the term "standard hybridization conditions" refers to a Tm of 55° C., and utilizes conditions as set forth above. In a preferred embodiment, the Tm is 60° C. In a more preferred embodiment, the Tm is 65° C. In a specific embodiment, "high stringency" refers to hybridization and/or washing conditions at 68° C. in 0.2×SSC, at 42° C. in 50% formamide, 4×SSC, or under conditions that afford levels of hybridization equivalent to those observed under either of these two conditions.

The present invention further relates to vectors for cloning and/or expression comprising a nucleic acid sequence of the invention and to host cell comprising the nucleic acid of the invention or said vector, i.e. a host cell wherein at least one of these vectors was transferred. The expression vector according to the invention comprises a nucleic acid sequence encoding a peptide, including a peptide derivative, or protein of the invention, said nucleic acid sequence being operably linked to elements allowing its expression. Said vector advantageously contains a promoter sequence, signals for initiation and termination of translation, as well as appropriate regions for regulation of translation. Its insertion into the host cell may be transient or stable. Said vector may also contain specific signals for secretion of the translated protein.

These various control signals are selected according to the host cell and may be inserted into vectors which self-replicate in the selected host cell, or into vectors which integrate the genome of said host.

Host cells may be prokaryotic or eukaryotic, including but not limited to bacteria, yeasts, plant cells, insect cells, mammalian cells, including cell lines which are commercially available. Preferred examples for host cells are COS-1, HEK cells, 293 cells, or CHO cells.

A subject of the present invention is also a method for producing a recombinant BPLP-peptide, wherein said host cell is transfected with said expression vector and is cultured under conditions allowing the expression of a BPLP-peptide. The transfection of the host cell may be performed using any standard technique, such as electroporation or phosphate calcium precipitation or Lipofectine®.

The protein or peptide can then be collected and purified, by means of well-known procedures for purification: the recombinant peptide or protein may be purified from lysates or cell extracts, from the supernatant of the culture medium, by methods such as HPLC chromatography, immunoaffinity techniques with specific antibodies, and the like.

The present invention further relates to methods of in vitro prognosis and/or diagnosis wherein the nucleic acid sequences of the invention or probes or primers derived thereof are used to detect aberrant synthesis, including abnormal high or low synthesis, or genetic abnormalities at the BPLP gene level.

The invention thus provides an in vitro method for prognosis and/or diagnosis of a condition involving an altered production of BPLP or of any of its maturation products, which method comprises detecting in a biological sample of a test subject, an abnormality in terms of quality and/or quantity in the BPLP gene or in its transcript.

The term "prognosis" refers to the determination or confirmation of a likelihood of a disease or condition to arise.

The present invention is more particularly directed to a method for detecting an abnormality in the BPLP gene comprising the steps of:
contacting a biological sample containing DNA with specific oligonucleotides permitting the amplification of all or part of the BPLP gene, the DNA contained in the sample having being rendered accessible, where appropriate, to hybridization, and under conditions permitting a hybridization of the primers with the DNA contained in the biological sample;
amplifying said DNA;
detecting the amplification products;
comparing the amplified products as obtained to the amplified products obtained with a normal control biological sample, and thereby detecting a possible abnormality in the BPLP gene.

The method of the invention can also be applied to the detection of an abnormality in the transcript of the BPLP gene, by amplifying the mRNAs contained in a biological sample, for example by RT-PCR.

Thus another subject of the present invention is a method for detecting an abnormality in the BPLP transcript, as previously defined comprising the steps of:
producing cDNA from mRNA contained in a biological sample;
contacting said cDNA with specific oligonucleotides permitting the amplification of all or part of the transcript of the BPLP gene, under conditions permitting a hybridization of the primers with said cDNA;
amplifying said cDNA;
detecting the amplification products;
comparing the amplified products as obtained to the amplified products obtained with a normal control biological sample, and thereby detecting a possible abnormality in the transcript of the BPLP gene.

This comparison of the amplified products obtained from the biological sample with the amplified products obtained with a normal biological sample is a quantitative comparison and/or a qualitative comparison. In this latter case, comparison can be carried out for example by specific probe hybridization, by sequencing or by restriction site analysis.

One skilled in the art very well knows the standard methods for analysing the DNA contained in a biological sample and for diagnosing a genetic disorder. Many strategies for genotypic analysis are available.

Preferably, one can use the DGGE method (Denaturing Gradient Gel Electrophoresis), or the SSCP method (Single Strand Conformation Polymorphism) for detecting an abnormality in the BPLP gene. Such methods are preferably followed by direct sequencing. The RT-PCR method may be advantageously used for detecting abnormalities in the BPLP transcript, as it allows to visualize the consequences of a splicing mutation such as exon skipping or aberrant splicing due to the activation of a cryptic site. This method is preferably followed by direct sequencing as well. The more recently developed technique using DNA chip can also be advantageously implemented for detecting an abnormality in the BPLP gene.

These methods for detecting an abnormality in the BPLP gene, or in its transcript, are particularly useful to identify mutations that result in nonfunctional BPLP protein or maturation products, and are advantageous for in vitro prognosis and/or diagnosis of diseases, wherein the BPLP gene is involved.

Examples of such diseases are diseases cited in the "therapeutic application" section.

Antibodies and Methods of Detection

The present invention further provides antibodies, specifically directed against (i.e. that specifically recognizes) the BPLP protein. The present invention further provides antibodies, specifically directed against (i.e. that specifically recognizes) the peptides as above defined, including peptides derivatives.

Accordingly, the present invention provides antibodies directed against peptides derived from human BPLP protein, and peptide derivatives thereof.

More particularly, the present invention provides antibodies directed against peptides which comprise, consist essentially of, or consist of sequence X1-X2-Arg-Phe-Ser-Arg (SEQ ID NO: 6) as above defined. When the peptide of the invention comprises or consists essentially of sequence X1-X2-Arg-Phe-Ser-Arg (SEQ ID NO: 6), said sequence is the C-terminal part of the peptide of the invention. In preferred embodiments, the present invention provides antibodies directed against (i.e. that specifically recognize) peptides which comprise, consist essentially of, or consist of sequence QRFSR (SEQ ID NO: 3). In a most preferred embodiment, the present invention provides antibodies directed against (i.e. that specifically recognize) QRFSR (SEQ ID NO: 3) or antibodies directed against (i.e. that specifically recognize) YQRFSR (SEQ ID NO: 4) or antibodies directed against (i.e. that specifically recognize) CQRFSR (SEQ ID NO: 5).

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')2 and F(v).

Antibodies that inhibit the interaction of a BPLP maturation product or a peptide derivative thereof with its receptor are more particularly useful.

Whereas polyclonal antibodies may be used, monoclonal antibodies are preferred for they are more reproducible in the long run.

Procedures for raising polyclonal antibodies are also well known. Typically, such antibodies can be raised by administering the protein or peptide, including conjugate peptide, of the present invention subcutaneously to New Zealand white rabbits which have first been bled to obtain pre-immune serum. The antigens can be injected at a total volume of 50 μl per site at ten different sites or at least five different sites. The rabbits are then bled five weeks after the first injection and periodically boosted with the same antigen administered subcutaneously at five fold lower concentration than the primary injection at maximum depending on quality of the immune response three times every six weeks. A sample of serum is then collected every 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, Antibodies: A Laboratory Manual, Cold Spring Harbor Laboratory, New York (1988).

A "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody.

Laboratory methods for preparing monoclonal antibodies are well known in the art (see, for example, Harlow et al., supra). Monoclonal antibodies (Mabs) may be prepared by immunizing a mammal, e.g. a mouse, rat, rabbit, goat, human and the like, against the purified BPLP protein, BPLP maturation products or peptide derivatives thereof, including conjugated BPLP-peptides. The antibody-producing cells in the immunized mammal are isolated and fused with myeloma or heteromyeloma cells to produce hybrid cells (hybridoma). The hybridoma cells producing the monoclonal antibodies are used as a source of the desired monoclonal antibody.

While Mabs can be produced by hybridoma culture, the invention is not to be so limited. Also contemplated is the use of Mabs produced by an expressing nucleic acid cloned from a hybridoma. That is, the nucleic acid expressing the molecules secreted by a hybridoma can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. In addition, the literature provides methods for forming chimeric antibodies, humanized antibodies, single chain antibodies and the like variations on a basic immunoreactive antibody fragment. All of these are considered within the scope of the invention insofar as a class and specificity of antibody is disclosed and claimed, regardless of the precise variant structure that one skilled in the art may construct.

The present invention further relates to an in vitro method for diagnosis, prognosis or determination of the evolution of a condition involving an altered production (i.e. a decrease or an increase of production in comparison to a control subject) of BPLP or of any of its maturation products. The method comprises detecting, or quantifying in a biological sample of a test subject, a BPLP protein or maturation products thereof, especially QRFSR (SEQ ID NO: 3), compared with the same in a biological sample of a control subject.

Examples of such conditions are diseases cited in the "therapeutic applications" section.

A "biological sample" is a fluid from a subject, including serum, blood, spinal fluid, cerebrospinal fluid, urine, milk, saliva or a tissue extract or a tissue or organ biopsy such as brain, spinal cord, bone tissue, kidney, prostate, placenta, dental tissue, glandular mucosa of stomach, intestine, salivary gland tissue, mammary glands, for example.

"A subject" or "a patient" is a vertebrate, e.g. a mammal, preferably a human being, regardless of his/her age, sex and general condition. Children and infants are also encompassed. The test subject may be asymptomatic, may be considered likely to develop the disease or condition. Subjects with a suspicion of a target disorder or subjects who have already shown symptoms of the disease or condition can also be tested.

The "control subject" may be a healthy subject or a subject without any apparent disorder that can involve the BPLP protein or one of its maturation products. In order to determine the evolution of a condition involving the BPLP protein or one of its maturation products, it may be very useful to test a subject for the expression of BPLP protein or a maturation products thereof, and to monitor the effect of a drug or the spreading of the condition, by testing him/her a second time, e.g. a few weeks later. In that case the results of the second test are compared with the results of the first test, and in general also with the results obtained with a "healthy" subject. The "control subject" then refers either to the same test subject or to a "healthy subject".

The term "diagnosis" refers to the determination or the confirmation of a disease or condition in a subject.

The term "prognosis" refers to the determination or confirmation of a likelihood of a disease or condition to arise.

The "expression or production of a BPLP protein or a maturation product thereof" may be determined by assaying the BPLP protein or a maturation products thereof.

Such assay methods comprise contacting a biological sample with a binding partner capable of selectively interacting with a BPLP protein or maturation products thereof, especially QRFSR (SEQ ID NO: 3), present in the sample. The binding partner is generally an antibody, that may be polyclonal or monoclonal, preferably monoclonal.

Methods for producing antibodies as described above in accordance with therapy can also be easily adapted to produce antibodies useful for the diagnostic or prognostic methods according to the invention.

For example, the presence or production of BPLP protein or of any of its maturation products, or a mutated form of the protein or of the maturation product, can be detected by incubating a biological sample with an antibody that specifically recognizes the BPLP protein or an antibody that specifically recognizes a maturation product thereof, especially QRFSR (SEQ ID NO: 3), e.g. using standard electrophoretic and liquid or solid immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassay such as those using radioiodinated or tritiated BPLP protein or any of its maturation products, especially QRFSR (SEQ ID NO: 3); immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound BPLP protein or unbound maturation products thereof, especially unbound QRFSR (SEQ ID NO: 3), from the bound BPLP protein or maturation products, especially QHNPR (SEQ ID NO: 8), to the specific antibody which is immobilized on a solid phase. Solid supports which can be used in the practice of the invention include supports such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Thus, in one particular embodiment, the presence of bound BPLP protein or maturation products thereof, especially QRFSR (SEQ ID NO: 3), from a biological sample can be readily detected using a secondary binder comprising another antibody, that can be readily conjugated to a detectable enzyme label, such as horseradish peroxidase, alkaline phosphatase or urease, using methods known to those of skill in the art. An appropriate enzyme substrate is then used to generate a detectable signal, such as a chromogenic or fluorogenic signal for example. In other related embodiments, competitive-type ELISA techniques can be practiced using methods known to those skilled in the art.

The above-described assay reagents, including the antibodies, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Gene Therapy

In accordance with the present invention, the modulation of the membrane metallopeptidase activity may be achieved by modifying (i.e. increasing or decreasing) the amount of BPLP protein, maturation products thereof in the cells of a patient and release therefrom, or expressing and possibly releasing a peptide, including peptide derivative, as defined above. Increasing of the amount of BPLP protein or maturation products thereof in the cells of a patient and possibly release therefrom, expressing and possibly releasing a peptide as defined above including a peptide derivative, may be performed by transfecting the cells with BPLP expressing vector or a vector that expresses a BPLP protein, a BPLP maturation product or a peptide as defined above, including a peptide derivative, e.g. in the form of a naked DNA or as a viral vector.

Preferably, the nucleic acid of this invention forms part of a vector. Such vector is a nucleic acid comprising a coding sequence operatively associated with sequences that control expression of the protein or peptide in a cell transfected with the vector.

The use of such a vector indeed makes it possible to improve the administration of the nucleic acid into the cells of the subject and especially to the cells to be treated, and also to increase its stability in the said cells, which makes it possible to obtain a durable therapeutic effect. Furthermore, it is possible to introduce several nucleic acid sequences into the same vector, which also increases the efficacy of the treatment.

The vector used may be of diverse origin, as long as it is capable of transforming animal cells, preferably human cells. In a preferred embodiment of the invention, a viral vector is used which can be chosen from adenoviruses, retroviruses, adeno-associated viruses (AAV), lentivirus, herpes virus, cytomegalovirus (CMV), vaccinia virus and the like. Vectors derived from adenoviruses, retroviruses or AAVs, HIV-derived retroviral vectors, incorporating heterologous nucleic acid sequences have been described in the literature.

The present invention therefore also relates to any recombinant virus comprising, inserted into its genome, nucleic acid sequence that encodes the BPLP protein, a BPLP maturation product or a peptide as defined above, including a peptide derivative.

Advantageously, the recombinant virus according to the invention is a defective virus, devoid of at least the sequences necessary for the replication of the said virus in the infected cell.

It is particularly advantageous to use the nucleic acid sequences of the invention in a form incorporated in an adenovirus, an AAV or a defective recombinant retrovirus.

Targeted gene delivery is described in International Pat. Publication WO 95/28494, published October 1995.

Alternatively, the vector can be introduced in vivo by lipofection. For the past decade, there has been increasing use of liposomes for encapsulation and transfection of nucleic acids in vitro. Information regarding liposome is provided in the "pharmaceutical composition" section of the present application as well.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, Lipofectamine®, use of a gene gun, or use of a DNA vector transporter.

Pharmaceutical Compositions

The BPLP-peptides (that is to say the BPLP protein, peptides derived from BPLP, maturation products, peptides defined above, including peptide derivatives and mimetics), or the nucleic acids that encode such BPLP-peptides and antibodies against said BPLP-peptides can be formulated in pharmaceutical compositions in association with a pharmaceutically acceptable carrier. For instance the pharmaceutical compositions are suitable for a topical, oral, sublingual, parenteral, intranasal, intravenous, intramuscular, subcutaneous, transcutaneous or intraocular administration and the like.

A subject matter of the invention is also a pharmaceutical composition comprising a polymer of said BPLP-peptide or mimetic thereof.

Preferably, the nucleic acid forms part of a vector expressing said nucleic acid.

Preferably, the pharmaceutical compositions contain vehicles which are pharmaceutically acceptable for a formulation capable of being injected.

The suitable pharmaceutical compositions may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses of BPLP-peptide, antibodies or nucleic acid used for the administration can be adapted as a function of various parameters, and in particular as a function of the mode of administration used, of the relevant pathology, or alternatively of the desired duration of treatment.

To prepare pharmaceutical compositions for peptide therapy, an effective amount of the BPLP-peptide may be dissolved or dispersed in a pharmaceutically acceptable carrier or aqueous medium.

Examples of pharmaceutical formulations are provided hereafter.

Pharmaceutical compositions comprise an effective amount of the BPLP-peptide, nucleic acid or antibodies, in a pharmaceutically acceptable carrier or aqueous medium.

"Pharmaceutically" or "pharmaceutically acceptable" refer to molecular entities and compositions that do not produce an adverse, allergic or other untoward reaction when administered to an animal, including a human, as appropriate.

As used herein, a "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with a variety of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The BPLP-peptide of interest may be formulated within a therapeutic mixture to comprise about 0.0001 to 100 milligrams, or about 0.001 to 0.1 milligrams, or about 0.1 to 1.0 or even about 1 milligram to 10 milligrams or even about 10 to 100 milligrams per dose or so. Multiple doses can also be administered. Preferred dosages are from about 0.1 µg/kg to about 1 mg/kg, more preferably from about 1 µg/kg to about 100 µg/kg, and most preferably from about 10 µg/kg to about 100 µg/kg.

In addition to the formulations for parenteral administration, such as intravenous or intramuscular injection, other pharmaceutically acceptable forms include, e.g. tablets or other solids for oral administration; liposomal formulations; time release capsules; and any other form currently used, including creams.

Other routes of administration are contemplated, including nasal solutions or sprays, aerosols or inhalants, or vaginal or rectal suppositories and pessaries or cream, and long-acting delivery polymers.

In certain embodiments, the use of liposomes and/or nanoparticles is contemplated for the introduction of BPLP-peptide agents, as well as nucleic acid vectors or antibodies into host cells.

The invention also relates to pharmaceutical compositions above defined further comprising a second pharmaceutical agent that acts synergistically with BPLP-peptide.

Therapeutic Applications

The BPLP-peptides described above, antibodies against said BPLP-peptides or nucleic acids coding for said BPLP-peptides are useful in the prevention or treatment of diseases or disorders, wherein a modulation of the activity of a membrane metallo-ectopeptidase is sought, more particularly a membrane-zinc metallopeptidase, such as NEP and APN.

Natural NEP substrates are mainly the peptide hormones: Enkephalins, Substance P, Bradykinin, Angiotensin II and Atrial Natriuretic Peptide which play key role in the control of central and peripheral pain perception, inflammatory phenomena, mineral exchange and/or arterial tone (Roques et al., 1993).

More particularly, neutral endopeptidase, NEP 24-11, is distributed both in nervous and peripheral tissues of mammals, and in the periphery it is particularly abundant in the kidney and placenta. In these tissues the cell-surface metallopeptidase NEP participates in the postsecretory processing and metabolism of neuropeptides, systemic immunoregulatory peptides and peptide-hormones. By controlling the active levels of circulating or secreted regulatory peptides, NEP modulates their physiological receptor-mediated action. Hence, the membrane-anchored NEP is involved in regulating the activity of: potent vasoactive peptides such as Substance P, Bradykinin (BK), Atrial Natriuretic peptide (ANP), and Angiotensin II (AII); potent inflammatory/immunoregulatory peptides such as Substance P and BK and fMet-Leu-Phe (fMLP); potent opioid neuropeptides such as Met and Leu-Enkephalins (Enk) and potent mineral exchange and fluid homeostasis regulatory peptides such as ANP, C-type Natriuretic Peptide (CNP) and B-type Natriuretic Peptide (BNP). However the levels of these peptides are changed through the NEP-induced formation/degradation only in regions where they are tonically released or where their release is triggered by a stimulus.

From an integrative point of view, the NEP biological activity is to control the active levels of peptidergic signals involved in arterial tension regulation, in inflammatory phenomena and in water-mineral homeostasis, as well as, in the control of pain processing. From a clinical point of view, this substantiates the fact that NEP is an important drug target in various disease states. For example, by inhibiting NEP, thereby increasing the levels and duration of action of central or peripheral endogenous opioids, an analgesic effect or an anti-depressant effect could be obtained, or by inhibiting endogenous AII formation and substance P, BK and ANP inactivation, antihypertensive, natriuretic and diuretic agents could be obtained. The main advantage of modifying the concentrations of endogenous peptides by use of NEP inhibitors is that the pharmacological effects are induced only at receptor stimulated by the natural effectors, and are critically dependent on the tonic or stimulus-evoked release of the natural effectors happening upon environmental, behavioral and physiopathological stressful situations (Roques et al, 1993).

Examples of mammalian membrane metallopeptidases besides NEP are ECE (Endothelin-Converting Enzymes), in particular ECE1 and ECE2, the erythrocyte cell-surface antigen KELL and the product of PEX gene associated with X-linked hypophosphatemic rickets, as well as ACE (Angiotensin Converting Enzyme) and APN (Aminopeptidase N).

Inhibition of ACE and/or ECE has a significant application in the treatment of hypertension and the prevention and treatment of atherosclerosis.

Inhibition of APN in conjunction with NEP has significant application in the treatment of pain and depression.

Inhibition of related membrane metallopeptidases has therapeutic effects in the treatment of tumors, namely ovarian, colorectal, brain, lung, pancreas, gastric and melanoma cancers, and reducing the incidence of metastasis, atherosclerosis and/or hypertension. Inhibitions of related membrane metallopeptidases has also therapeutic effects in pain controlling. Such antinociceptive effects on acute pain are analgesic effects but also effects on chronic inflammatory pain such as arthritis or inflammatory bowel disease.

Furthermore, inhibition of bacterial or viral metallopeptidase is expected to have anti-infection effects.

Metallopeptidases playing an important role in pathogen host tissue invasion and immunological and inflammatory processes, for example those of *Streptococcus pyogenes, Pseudomonas aeruginosa, Porphyromonas gingivalis* and *Legionella pneumophila*.

Furthermore, bacterial metallopeptidases, especially zinc-metallopeptidases play an important role in the diseases caused by proteolytic toxins, such as the toxins of *B. anthracis* (Anthrax Lethal factor) and the neurotoxins of *C. tetanum* and *botulinum*.

Other metallopeptidases play an important role in various infections such as infections caused by HIV (FR 2 707 169).

The importance of proteinase inhibitors for the treatment of bacterial or viral diseases may be found in J. Potempa and J. Travis.

The different roles of metallopeptidases are disclosed in Turner et al, 2001; Kenny et al, 1977; Kenny et al, 1987; Beaumont et al, 1996.

One object of the present invention is the use of the above described therapeutic peptides or nucleic acids as analgesic agents or anti-depressant agents by inhibiting NEP and APN at peripheral, spinal and/or supraspinal levels and thereby increasing the levels and duration of action of central or peripheral endogenous opioids, including enkephalins.

The prevention or treatment of pain, especially acute and chronic pain, visceral inflammatory and neuropathic pain, is contemplated.

The prevention or treatment of any hydro-mineral imbalance is also an aim of the invention. Among target disorders one may cite bone, teeth, kidney, parathyroid, pancreas, intestine, stomach mucosa, prostate, and salivary gland disorders that are caused by hydro-mineral imbalance.

In particular, the disorder may be selected from the group consisting of hyper or hypo-parathyroidism, osteoporosis, pancreatitis, submandibular gland lithiasis, nephrolithiasis and osteodystrophy.

The prevention or treatment of impaired interpersonal and behavioural disorders is of further interest. Various mental disorders are described in WO 02/051434.

In particular the invention is drawn at any disorder selected from the group consisting of avoidance disorder, decreased awareness disorder, autistic disorder, attention deficit hyperactivity disorder, arousal disorder, hospitalism, impaired interpersonal functioning and relationship to the external world, schizoid personality disorder, schizophrenia, depressive disorder, decreased interest in environment, impaired social activity linked to sexuality, and impaired sexual behaviour, including untimely ejaculation and hyperactive sexual.

Diseases wherein a modulation of a membrane metallopeptidase is sought also include hypertension, aterosclerosis, tumor, inflammatory arthritis and bowel disease.

Treatment of infections is also encompassed. Especially, the importance of proteinase inhibitors for the treatment of bacterial or viral diseases may be found in J. Potempa and Travis.

The BPLP-peptides, antibodies or nucleic acids described above are also useful for controlling immuno-inflammatory responses.

The BPLP-peptides, antibodies or nucleic acids as defined above are also useful as a natriuretic agent or a diuretic agent.

Another object of the present invention is the use of the above described peptides or nucleic acids as a substitute in the treatment of drug abuse, notably morphine drug abuse.

Indeed, studies have suggested that the vulnerability to drug abuse and the development of reward and drug dependence is at least in part, a result of pre-existent or induced modifications and/or defect of the endogenous opioid system.

In this regard, using BPLP-peptide or nucleic acid to potentiate the effects of endogenous enkephalins will reduce the various side-effects (somatic signs of withdrawal) produced by interruption of chronic morphine or heroin administration.

According to the invention, reducing the inhibitory effect of the BPLP-peptides on NEP may be desired, e.g. by using an antibody against the BPLP protein or peptides. This enhancement of NEP activity is particularly advantageous in the treatment of neurodegenerative diseases such as a disease or disorder associated with amyloidosis. Indeed it has been shown that inhibitors of neprilysin (a neutral endopeptidase, NEP or enkephalinase) by synthetic inhibitor, raises amyloid β levels (Newell et al, 2003). Leissring et al, 2003 further reported that transgenic overexpression of neprilysin in neurons significantly reduces brain Aβ levels, retards or completely prevents amyloid plaque formation and its associated cytopathology, and rescues the premature lethality present in amyloid precursor protein transgenic mice.

A disease or disorder is associated with amyloidosis when amyloid deposits or amyloid plaques are found in or in proximity to tissues affected by the disease, or when the disease is characterized by overproduction of a protein that is or can become insoluble. The amyloid plaques may provoke pathological effects directly or indirectly by known or unknown mechanisms. Examples of amyloid diseases include, but are not limited to, systemic diseases, such as chronic inflammatory illnesses, multiple myeloma, macroglobulinemia, familial amyloid polyneuropathy (Portuguese) and cardiomyopathy (Danish), systemic senile amyloidosis, familial amyloid polynephropathy (Iowa), familial amyloidosis (Finnish), Gerstmann-Straussler-Scheinker syndrome, familial amyloid nephropathy with urticaria and deafness (Muckle-Wells syndrome), medullary carcinoma of thyroid, isolated atrial amyloid, and hemodialysis-associated amyloidosis (HAA); and neurodegenerative diseases.

The term "neurodegenerative disease" refers to a disease or disorder of the nervous system, particularly involving the brain, that manifests with symptoms characteristic of brain or nerve dysfunction, e.g., short-term or long-term memory lapse or defects, dementia, cognition defects, balance and coordination problems, and emotional and behavioral deficiencies. The present invention is more particularly concerned with neurodegenerative diseases that are associated with amyloidosis. Such diseases are "associated with amyloidosis" when histopathological (biopsy) samples of brain tissue from subjects who demonstrate such symptoms would reveal amyloid plaque formation. As biopsy samples from brain, especially human brain, are obtained with great difficulty from living subjects or might not be available at all, often the association of a symptom or symptoms of neurodegenerative disease with amyloidosis is based on criteria other than the presence of amyloid deposits, such as plaques or fibrils, in a biopsy sample.

In a specific embodiment, according to the present invention the neurodegenerative disease is Alzheimer's disease (AD). In other embodiments, the disease may be the rare Swedish disease characterized by a double KM to NL mutation in amyloid precursor protein (APP) near the aminoterminus of the βAP portion of APP. Another such disease is hereditary cerebral hemorrhage with amyloidosis (HCHA or HCHWA)-Dutch type. Other such diseases known in the art and within the scope of the present invention include, but are not limited to, sporadic cerebral amyloid angiopathy, hereditary cerebral amyloid angiopathy, Down's syndrome, Parkinson-dementia of Guam, and age-related asymptomatic amyloid angiopathy.

In a further aspect, the neurodegenerative disease is a subacute spongiform encephalopathy, such as but not limited to, scrapie, Creutzfeldt-Jakob disease, Gerstmann-Straussler disease, kuru, chronic wasting disease of mule-deer and elk, bovine spongiform encephalopathy of cattle, and mink transmissible encephalopathy.

The invention further relates to the use of an agent that modulates the interaction between endogenous BPLP protein or maturation product, e.g. QRFSR (SEQ ID NO: 3), and a membrane metallopeptidase for the preparation of a therapeutic composition for preventing or treating diseases wherein a modulation of the activity of said membrane metallopeptidase is sought.

Screening Methods

The methods that allow a person skilled in the art to select and purify candidate compounds that bind to the same targets and have an agonist or an antagonist biological activity of the BPLP protein or maturation products thereof, e.g. the QRFSR peptide (SEQ ID NO: 3), are described hereunder.

The candidate compound may be a protein, a peptide, a hormone, an antibody or a synthetic compound which is either a peptide or a non peptidic molecule, such as any compound that can be synthesized by the conventional methods of organic chemistry.

The invention provides an in vitro method for screening compounds for their ability to bind to the NEP binding site for the BPLP protein or a maturation product thereof, e.g. the QRFSR peptide (SEQ ID NO: 3), comprising the steps of:

a) incubating a candidate compound with a NEP expressing cell, in the presence of the BPLP protein or a maturation product thereof, e.g. the QRFSR peptide (SEQ ID NO: 3), or any peptide retaining the binding specificity or the physiological activity of BPLP protein or of its maturation products, e.g. the peptide YQRFSR (SEQ ID NO: 4);

b) determining the ability of the candidate compound to compete with the BPLP protein or a maturation product thereof, e.g. the QRFSR peptide (SE) ID NO: 3) or with the peptide retaining the binding specificity or the physiological activity of BPLP protein or of its maturation products, e.g. the peptide YQRFSR (SEQ ID NO: 4), for binding to NEP.

Binding assays of the candidate compound are generally performed at 4° C. to 25° C. or 37° C.

The NEP expressing cell may be in a cell culture, such as a confluent target cell culture monolayer, or a target organ specimen or a tissue sample (e.g. cyrosections, slices, membrane preparations or crude homogenates) that contains NEP binding sites for the BPLP protein or a maturation product thereof, e.g. the QRFSR peptide (SEQ ID NO: 3).

A preferred tissue sample that is used in the screening methods according to the present invention is a membrane preparation or slices of spinal cord from a mammal, a tissue known to be appropriated for NEP activity measurement.

Other preferred tissue samples that can be used in the screening methods according to the present invention are all peripheral tissue preparations that are known to be enriched in NEP-peptidase and/or to be targets for the BPLP protein or a maturation product thereof, e.g. the QRFSR peptide (SEQ ID NO: 3). For example one may use mammal renal outer medulla, placenta, testis, prostate and bone. For example, such a procedure can be applied to tissues and/or cells of mouse, rat or human origin or cell lines transfected with metallo-ectopeptidase cDNA, in particular NEP cDNA, especially human NEP cDNA.

The BPLP-protein or maturation product thereof (or the peptide that retains the binding specificity or the physiological activity of the BPLP protein or of its matured products) is preferably labeled, e.g. by a radioactive ($^{32}$P, $^{35}$S, $^{3}$H, $^{125}$I etc. ...) or non-radioactive label (digoxigenin, CyDye-europium, fluorescein etc.). It is then incubated with the NEP expressing cell during a time sufficient and under conditions for the specific binding to take place.

The label specifically bound to the cell may then be quantified in the presence of various concentrations of said candidate compound, for example from $10^{-10}$ to $10^{-5}$ M.

Accordingly, the present invention further provides a process for screening a compound that specifically bind to the NEP binding sites for the BPLP protein, or maturation product thereof comprising the steps of:

a) preparing a cell culture or preparing an organ specimen or a tissue sample (such as cryosections or slices or membrane preparations or crude homogenates) containing NEP binding sites for the BPLP protein or maturation products thereof;

b) adding the candidate compound to be tested in competition with half-saturation concentration of labeled protein or maturation product thereof (or a peptide that retains the binding specificity or the physiological activity of the BPLP protein or of its matured products);

c) incubating the cell culture, organ specimen or tissue sample of step a) in the presence of the candidate compound during a time sufficient and under conditions for the specific binding to take place;

d) quantifying the label specifically bound to the cell culture, organ specimen or tissue sample in the presence of various concentrations of candidate compound (preferably $10^{-10}$ to $10^{-5}$ M).

In said above process, a half saturating concentration is the concentration of the labeled BPLP protein or maturation product thereof, e.g. the QRFSR peptide (SEQ ID NO: 3) (or the peptide that retains the binding specificity or the physiological activity of the BPLP protein or of its matured products) which binds 50% of the NEP binding sites.

This process also allows to define the relative affinity of the candidate compound compared to the BPLP protein, or maturation products, e.g. QRFSR (SEQ ID NO: 3) affinity (or the peptide that retains the binding specificity or the physiological activity of the BPLP protein or of its matured products).

Another object of the present invention is a process for determining the relative affinity of ligand compounds that specifically bind to the NEP binding sites for the BPLP protein, or maturation products, (or the peptide that retains the binding specificity or the physiological activity of the BPLP protein or of its matured products), said process comprising the steps a), b), c) and d) of the above process for each candidate compound and further comprising the step e) of comparing the affinity of each candidate compound quantified in step d) to the one of the other candidate compounds.

Another object of the present invention is a process for determining the affinity of a compound that specifically binds to the NEP binding site for the BPLP protein or maturation products thereof, comprising the steps of:

a) preparing a cell culture or preparing an organ specimen or a tissue sample (such as cryosections or slices or membrane preparations or crude homogenates) containing NEP binding sites for the BPLP protein or maturation products thereof;

b) adding the candidate compound which has previously been labeled with a radioactive or a nonradioactive label;

c) incubating the cell culture, organ specimen or tissue sample of step a) in the presence of the labeled candidate compound during a time sufficient and under conditions for the specific binding to take place; and d) quantifying the label specifically bound to the cell culture, organ specimen or tissue sample in the presence of various concentrations of the labeled candidate compound (preferably $10^{-10}$ to $10^{-5}$ M).

The candidate compound is preferably labeled, e.g. by a radioactive ($^{32}$P, $^{35}$S, $^{3}$H, $^{125}$I etc....) or non-radioactive label (digoxigenin, CyDye-europium, fluorescein etc.). It is then incubated with the NEP expressing cell during a time sufficient and under conditions for the specific binding to take place.

One may further compare the affinity of each candidate compound quantified to the one of the other candidate compounds, so that the relative affinity of candidate compound that specifically binds to the NEP binding site for the BPLP protein or a maturation product thereof, e.g. the QRFSR peptide (SEQ ED NO: 3), is determined.

The invention further provides an in vitro method for screening compounds for their ability to act as agonists or antagonists of the BPLP protein or maturation products thereof on NEP activity, which method comprises the steps of:

a) incubating a candidate compound with a NEP expressing cell, in the presence of (i) the BPLP protein or a maturation product thereof, e.g. the QRFSR peptide (SEQ ID NO: 3), or any peptide retaining the binding specificity or the physiological activity of the BPLP protein or of its matured products, and (ii) a NEP substrate;

b) determining the endoproteolysis of the NEP substrate by the NEP, wherein an increased endoproteolysis in the presence of the candidate compound, in comparison with the endoproteolysis in the absence of the candidate compound, is indicative of an antagonist activity; while a decreased endoproteolysis in the presence of the candidate compound, in comparison with the endoproteolysis in the absence of the candidate compound, is indicative of an agonist activity.

As used herein, an agonist of a BPLP protein or maturation product thereof is a molecule which has the ability to inhibit a metallo-ectopeptidase activity, especially NEP or APN activity.

As used herein, an antagonist of a BPLP protein or maturation product thereof is a molecule which has the ability to increase a metallo-peptidase activity, especially NEP or APN activity.

Furthermore, the agonist or antagonist activity of the candidate compound can be assessed in determining the metabolic changes induced by this candidate compound on its target, such as the synthesis and/or release of the primary or secondary messenger metabolites as a result of a transduction signal via the protein kinases or adenylate cyclase and the activation of a protein of the G family.

In particular embodiments, the present invention also pertains to a process for screening a compound that is an agonist of the BPLP protein or a maturation product thereof, comprising the steps of:

a) preparing a cell culture or preparing an organ specimen or a tissue sample (such as cryosections or slices or membrane preparations or crude homogenates) containing NEP binding sites for the BPLP protein or a maturation product thereof;

b) incubating the cell culture, organ specimen or tissue sample of step a) at concentrations allowing measurement of NEP enzymatic activity in the presence of the candidate compound (preferably $10^{-10}$ to $10^{-5}$ M), a half-saturating concentration of the BPLP protein or a maturation product thereof (or any peptide retaining the binding specificity or the physiological activity of the BPLP protein or of its matured products) and a NEP substrate during a time sufficient for the endoproteolysis of the NEP substrate to take place under initial velocity conditions;

c) quantifying the activity of the NEP present in the biological material of step a) by measuring the levels of NEP substrate endoproteolysis, respectively in the presence or in the absence of the candidate compound and in the presence or in the absence of the BPLP protein or a maturation product thereof, or the peptide retaining the binding specificity or the physiological activity of the BPLP protein or of its matured products.

In said above process, a half-saturating concentration is the concentration of the BPLP protein or a maturation product thereof which results in a reduction by half of the degradation of the NEP substrate.

Another object of the present invention comprises a process for screening a compound that is an antagonist of the BPLP protein or a maturation product thereof, comprising the steps of:

a) preparing a cell culture or preparing an organ specimen or a tissue sample (cryosections or slices or membrane preparations or crude homogenates) containing NEP binding sites for the BPLP protein or a maturation product thereof;

b) incubating the cell culture, organ specimen or tissue sample of step a) at concentrations allowing measurement of NEP enzymatic activity under initial velocity conditions in the presence of a submaximal concentration of the BPLP protein or a maturation product thereof (or any peptide retaining the binding specificity or the physiological activity of the BPLP protein or of its matured products) and a NEP substrate, in the presence of the candidate compound during a time sufficient for the endoproteolysis of the NEP substrate to take place under initial velocity conditions;

c) quantifying the activity of the NEP present in the biological material of step a) by measuring the levels of NEP substrate endoproteolysis, respectively in the presence or in the absence of the candidate compound and in the presence or in the absence of the BPLP protein or a maturation product thereof, or the peptide retaining the binding specificity or the physiological activity of the BPLP protein or of its matured products.

In a preferred embodiment of said above process, a submaximal concentration is a concentration of peptide which results in a reduction by at least 50% and preferably by at least 75% of the degradation of the substrate.

The below examples and figures illustrate the invention without limiting its scope.

LEGENDS TO THE FIGURES

FIG. 1 shows representative cation-exchange HPLC profile of $^3$H-YQRFSR (SEQ ID NO: 4) marker added to 2.5 ml salivary methanol-acid extract corresponding to 2.5 ml human saliva. The recovery of the major radioactive peak was evaluated at 75-84% (dotted bars).

FIG. 2 shows representative cation-exchange HPLC profile of a salivary methanol-acid extract obtained from 7 ml human saliva. Fractions were analyzed for their inhibitory potency of substance P endoproteolysis by human ecto-endopeptidase activity (LNCaP cell line).

FIG. 8 is a RP-HPLC chromatographic analysis of the YQRFSR peptide (SEQ ID NO: 4). The YQRFSR peptide (SEQ ID NO: 4) (175 µM) was not metabolized by human cell surface endopeptidases, in vitro, whilst it inhibited by 70% the substance P endoproteolysis mediated by human NEP ectoendopeptidase. The RP-HPLC chromatographic characteristics revealed that:

1/ the YQRFSR peptide (SEQ ID NO: 4) is not metabolized by human cell membranes containing NEP; 93% was recovered as intact peptide against 94% in absence of metabolizing membranes;

2/ in the same experimental conditions the YQRFSR peptide (SEQ ID NO: 4) inhibits by 70% the endoproteolysis of substance P by these human cell membranes.

Figure 9:
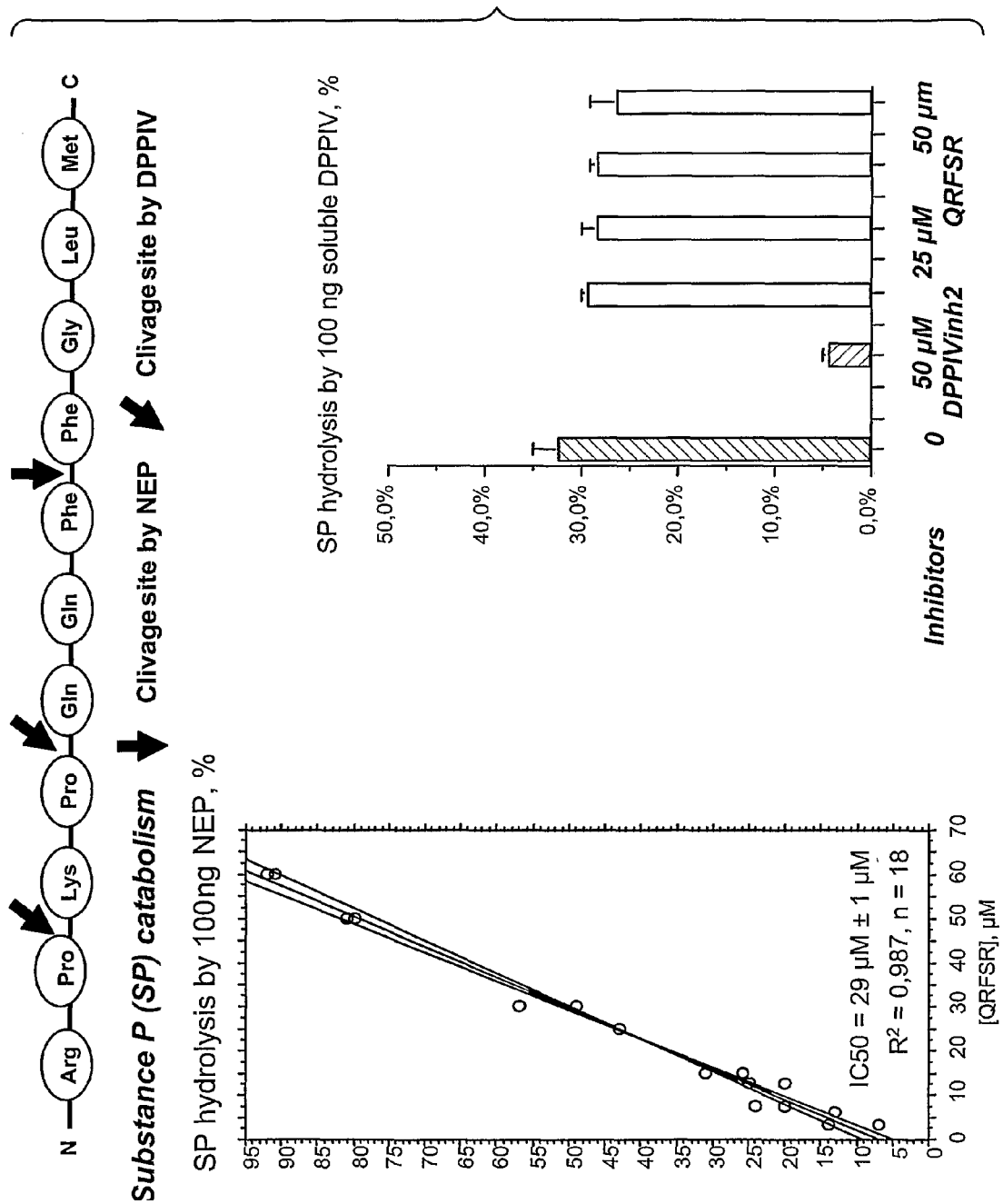

FIG. 9 shows the inhibitory effect of QRFSR-peptide (SEQ ID NO: 3) on the breakdown of substance P by recombinant human NEP. Concentration-dependent inhibitory effect of QRFSR-Peptide (SEQ ID NO: 3) on soluble recombinant human NEP activity and no effect of QRFSR-peptide (SEQ ID NO: 3) on the endoproteolysis of substance P by soluble recombinant hDPPIV activity.

Figure 10:
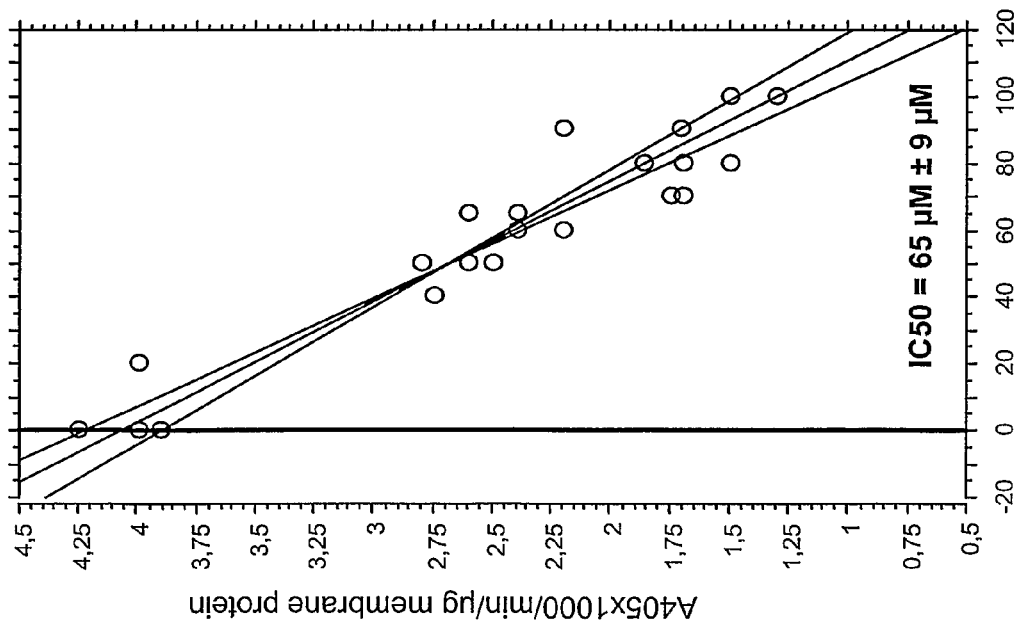

FIG. 10 shows the inhibitory effect of QRFSR-peptide (SEQ ID NO: 3) on the breakdown of APN synthetic substrate by cell surface human APN. Concentration-dependent inhibition by QRFSR-peptide (SEQ ID NO: 3) of the cleavage of Ala-pNA chromogenic substrate by cell surface HEK-hAPN.

Figure 11:
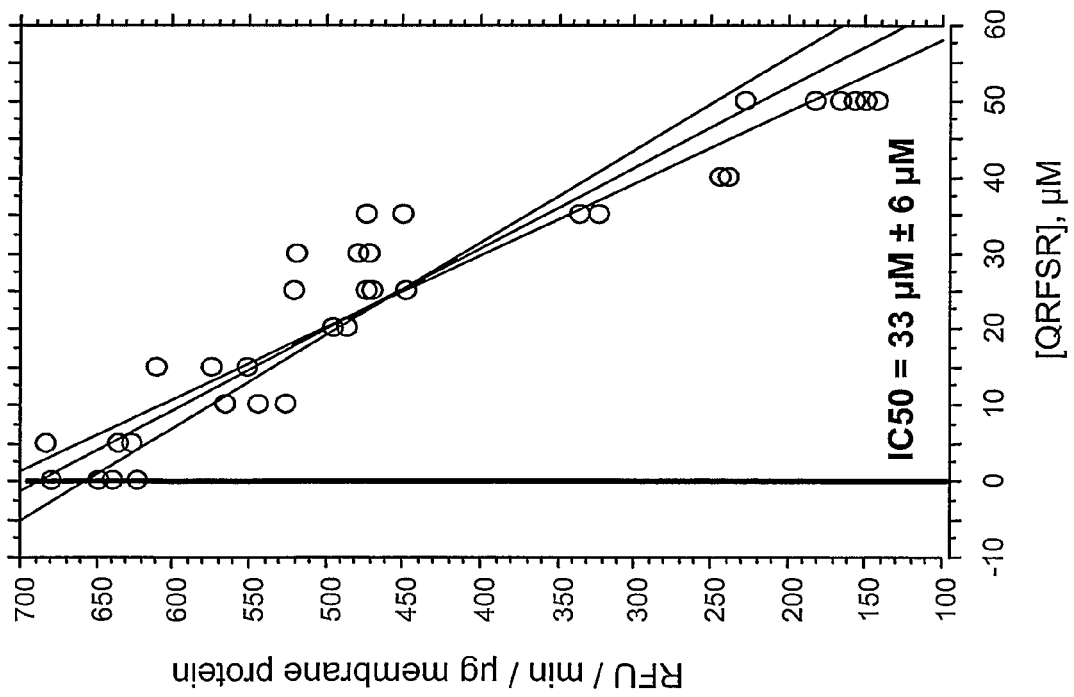

FIG. 11 shows the inhibitory effect of QRFSR-peptide (SEQ ID NO: 3) on the breakdown of NEP synthetic substrate by cell surface human NEP. Concentration-dependent inhibition by QRFSR-peptide (SEQ ID NO: 3) of the cleavage of Mca-BK2 fluorogenic substrate by cell surface HEK-hNEP.

Figure 12:
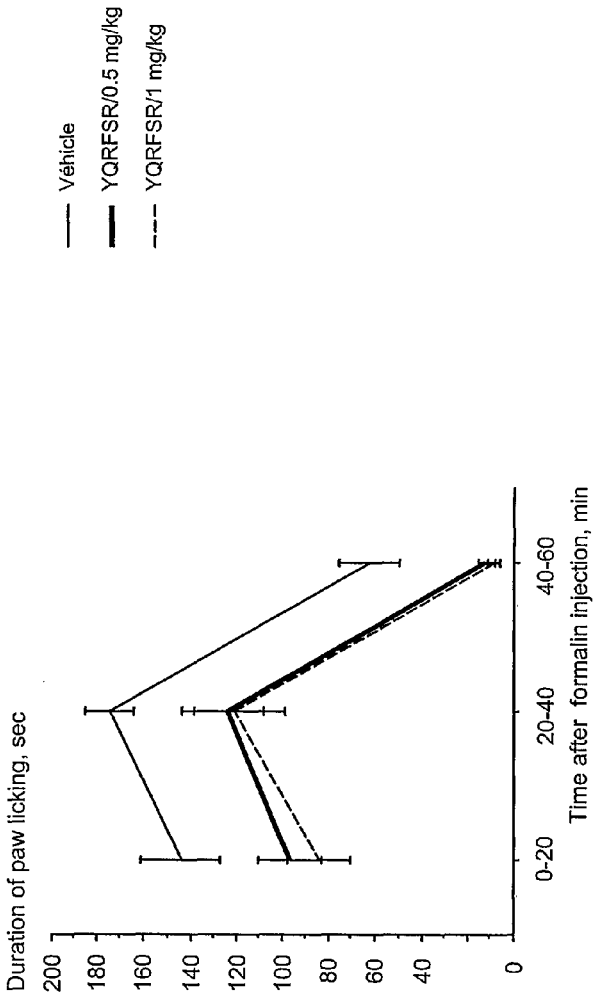

FIG. 12 shows the in vivo effect of YQRFSR-peptide (SEQ ID NO: 4) on the time spent by rat in paw licking of the formalin-injected hind paw; Mean±SEM.

Figure 13:
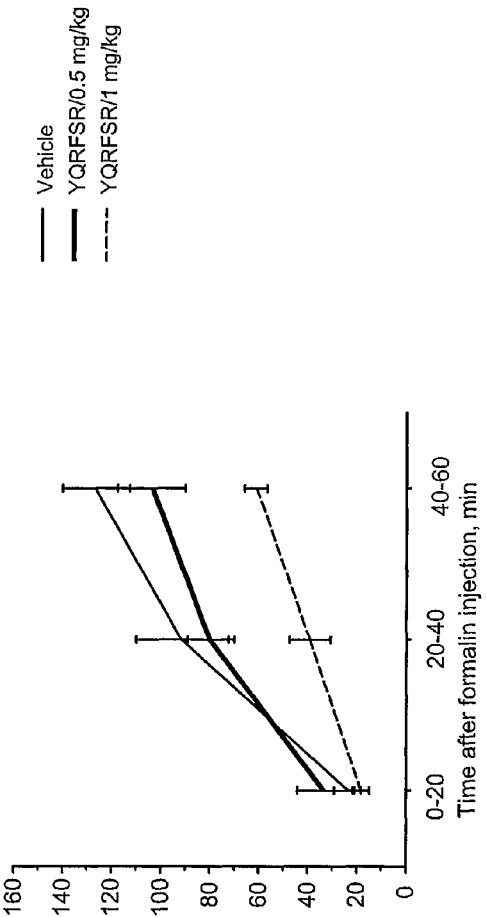

FIG. 13 shows the in vivo effect of YQRFSR-peptide (SEQ ID NO: 4) on the number of pain spasms following hind paw formalin injection; Mean±SEM.

Figure 14:
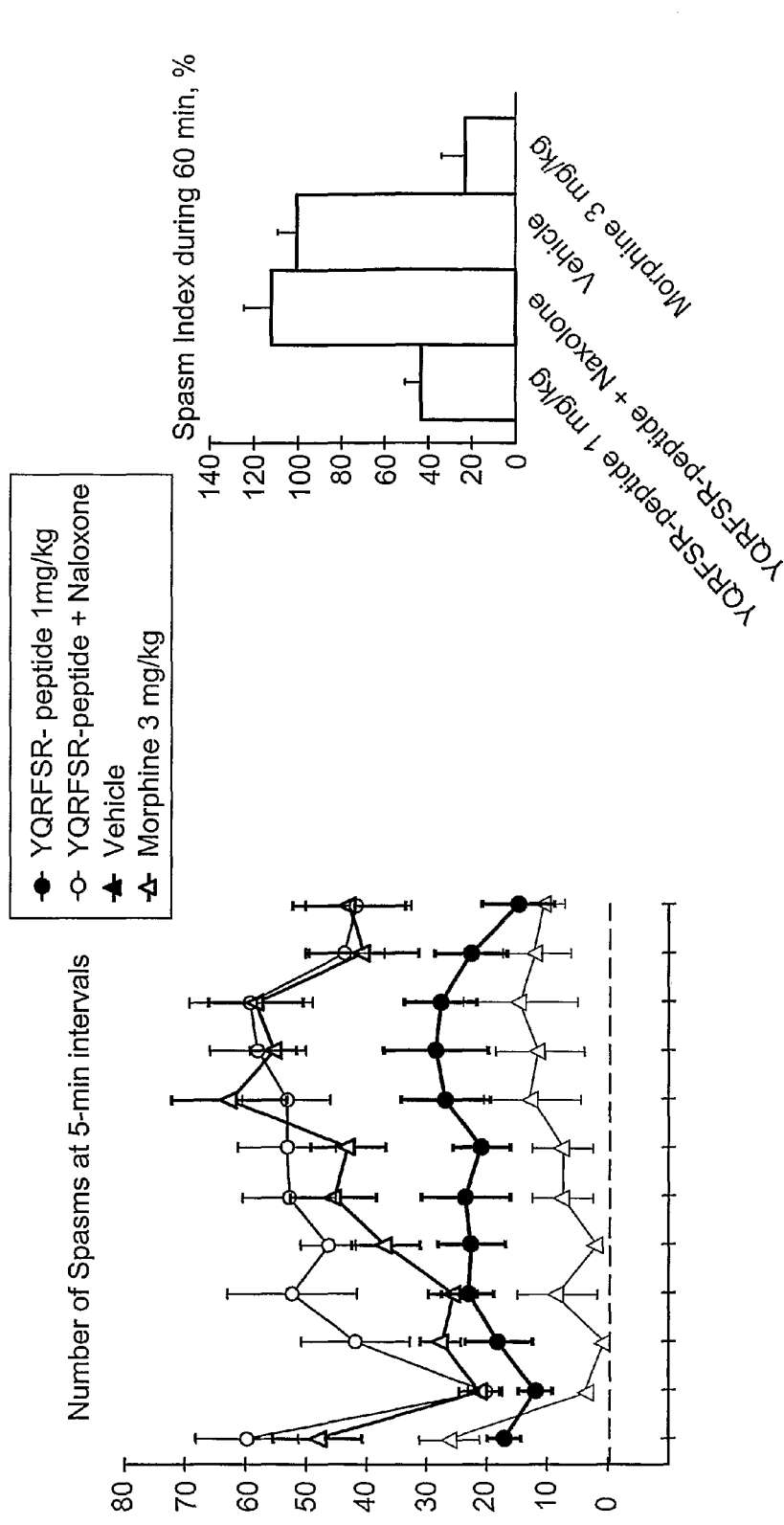

FIG. 14 shows the in vivo effect of YQRFSR-peptide (SEQ ID NO: 4) on the index of pain spasms during the 60 minute post injection of formalin. The analgesia induced by QRFSR-derived peptide (SEQ ID NO: 3) requires the activation of endogenous opioid receptors.

EXAMPLES

The study was designed to search natural metallo-ectopeptidases, especially NEP and/or APN inhibitor particularly in the human salivary secretions. The strategy for the detection and isolation of this product was based on the isolation of salivary low-molecular-mass components, which inhibit the endoproteolysis of NEP-sensitive substrate by human cells expressing the membrane-anchored human NEP. The inventors have developed the models of functional detection (membranes preparations of LNCaP and HEK human cells expressing NEP) and of molecular isolation (HPLC chromatography systems), for the identification by sequence analysis of the natural endogenous NEP ectopeptidase inhibitor(s) in human, i.e., the endogenous salivary functional homologue(s) of the rat sialorphin.

Example 1

Human Saliva Preparation

The protocol of clinical research established with the "centre de recherche Vaccinale et Biomedicale" of the Pasteur Institute, assession number: 2045, received the agreement of the CCPPRB committee (PARIS-COCHIN) and samplings of the human saliva from 10 healthy male volunteers, began in May 2003 and continued in October 2003. The saliva was collected into previously cooled "microsorp" tubes containing aprotinin (1000 KIU/ml) Pefabloc (0.4 mM) and HCl (0.1N) final concentration; this medium assuming to inhibit proteolysis activities. Thus saliva samples were stored at −80° C. until the methanol-extraction procedure was performed.

Example 2

Materials and Experimental Models for NEP Inhibition

1—Sources of Human Ectopeptidases NEP and APN:

Several Human cell lines have been described as expressing NEP as well as other members of the metalloecto-peptidase family; among them there are an osteoblaste cell line, MG-63 (osteosarcoma), a trophoblaste cell line, BeWo (placental choriocarcinoma), an prostate epithelial cell line, LNCaP (adenocarcinoma) and an enterocyte cell line, Caco-2 (colorectal adenocarcinoma). Culture conditions in defined medium useful for the cellular pharmacology analyses were first developed. Secondly, the inventors have confirmed by using Northern blot and immunocytochemical analyses that the LNCaP and BeWo were the only cell lines able to express NEP (ARNm and cell surface protein) in defined medium culture conditions (i.e., RPMI containing insulin, transferin and selenium, GIBCO) and after induction by DHT (dihydrotestosterone) and forskolin, respectively. And finally, in the experimental model of static incubations of membrane preparations originating from these cells, the inventors have defined the parameters allowing to analyze the human NEP-mediated endoproteolysis of substance P in the conditions of initial velocity measurement, i.e. 100 pM/min/μg LNCaP cell membrane proteins (10-fold lower specific activity for BeWo). The LNCaP membrane activity was inhibited in the presence of specific synthetic NEP inhibitor, such as thiorphan (62% for maximum inhibitory potency at 500 nM). In contrast, bestatin (25 μM) and captopril (10 μM) which block the aminopeptidase (APN, APB.) and angiotensin-converting enzyme (ACE) activities, respectively, did not inhibit the substance P hydrolysis by cell surface ectopeptidases; thus indicating that in the experimental conditions, the extra cellular breakdown of substance P was mainly caused by the NEP endopeptidase activity located at the surface of these cells.

In addition, in vitro model using the membrane preparations of transfected HEK cells with human NEP cDNA or human APN cDNA (HEK cells do not express these metalloectopeptidases) and soluble recombinant human NEP or soluble recombinant human DPP IV (Dipeptidylaminopeptidase IV) (without the N-terminal cytosol and transmembrane segment) have also been developed.

2—Substrates and Inhibitors:

In vitro, membrane amino- and endo-ectopeptidase activities of human cell membranes are assayed in vitro by measuring the breakdown of the following synthetic and natural substrates:

a/ Synthetic Specific Fluorogenic or Chromogenic Substrates:
Mca-R-P-P-G-F-S-A-F-K-(Dnp)-OH (SEQ ID NO: 12) and/or Suc-A-A-F-Amc (SEQ ID NO: 13) (NEP) (R&D systems and Bachem)
Ac-A-Amc or Ala-pNA(APN) (Bachem)

b/ Physiological Substrates:
Modified tritiated substance P[(3,4$^3$H)Pro$^2$-Sar$^9$-Met(O$_2$)$^{11}$]-Substance P (DuPont-NEN) and Native Substance P: R-P-K-P-Q-Q-F-F-G-L-M (SEQ ID NO: 14) (NEP-DPPIV-ACE) (Peninsula-Biovalley)
Native Met-enkephalin: Y-G-G-F-M (SEQ ID NO: 15) (NEP-APN) (Peninsula-Biovalley) Measuring the hydrolysis of these substrates by cell-membrane peptidases in the presence and absence of different available selective synthetic peptidase inhibitors assessed the specificity of the peptidase assay:
Thiorphan, Phosphoramidon (NEP) (Sigma and Roche)
Bestatin, Amastatin (APN) (Calbiochem)
DPPIV inhibitor II (DPPIV) (Calbiochem)
Captopril (ACE) (Sigma)

3—Measurement of Peptidase Activities

The ectopeptidase activities were measured according to the protocol developed and established for the functional characterization of the rat sialorphin (Rougeot et al., 2003). Briefly, for membrane preparations, the cells were homogenised at 4° C. in 10 volumes (vol./wt.) of 50 mM Tris/HCl buffered at pH 7.1. A first centrifugation at 1000×g and 5° C. for 5 min allows to remove the cellular debris and the nuclei in the pellet. A second centrifugation at 100 000×g and 5° C. for 30 min concentrates the membrane fraction in the pellet, which will be superficially washed three times in cold Tris/HCl buffer, resuspended in fresh buffer, aliquoted and stored at −80° C. while waiting to be used as enzyme source. Proteins determination was carried out using the Bio-Rad DC protein assay with Bovine Serum Albumin (BSA) as the standard.

Hydrolysis of substrates was measured by monitoring the metabolism rate in conditions of initial velocity measurement in the presence and absence of specific inhibitors. These were added to the preincubation medium. The standard reaction mixture consisted of cell membranes in a final volume of 200 μl Tris-HCl 50 mM pH 6.5-7.2. The substrate was added after preincubation for 10 min and the digestion carried out for 20 min at 25° C. in a constantly shaken water bath. The reaction was terminated by cooling to 4° C. and adding HCl (0.3N final concentration). The reaction tubes were then centrifuged (4700×g for 15 min at 4° C.) and the remaining intact substrate and its metabolites measured.

In the case of the use of natural substrates, substance P or Met-enkephalin, the products of the reaction are isolated and quantified according to their differential hydrophobic characteristics:
C-18 Sep-Pak cartridges (Waters) were used to analyse the hydrolysis of radiolabeled substance P. The $^3$H metabolites were isolated by elution with H2O-0.1% TFA and then with 25% methanol-0.1% TFA (4 ml each). The intact tritiated substrate was eluted with 75-100% methanol-0.1% TFA (4 ml).

RP-HPLC coupled to a spectrophotometer was used to analyse the hydrolysis of Met-enkephalin, (C-18 LUNA column, AIT). Elution with a 30-min linear gradient from 0.1% TFA in water to 0.1% TFA in 100% acetonitrile, at 1 ml/min, separated the two Met-enkephalin metabolites (YGG: 5.8±0.2; FM: 12.8±0.1 min retention time) and the intact substrate (YGGFM: 18.8±0.2 min). Their identities and relative quantities (peak height) were checked by monitoring the column outflow at 264 nm (L3000, Merck).

The disappearance of the initial Met-enkephalin substrate was also quantified by radioimmunoassay (RIA). The assay used anti-Met enkephalin antiserum (Gros et al., 1978) and $^{125}$I-Met-enkephalin (80 TBq/mmol, NEN); it detected nanomolar concentrations of Met-enkephalin in the presence of micromolar concentrations of Tyr-Gly-Gly and Phe-Met metabolites. The radioactivity of each fraction was determined by liquid scintillation spectrometry.

In the case of the use of synthetic substrates, the kinetics of appearance of the fluorescent signal (intensity and polarization) was directly analyzed by using a multi-well spectrofluorimeter; the intensity of the signal is directly proportional to the quantity of metabolites formed during the reaction.

Example 3

Human Saliva Purification and Chromatography

The protocol of extraction and purification of the human salivary components mimicked the one that was developed and established for the molecular characterization of the sialorphin from rat saliva (Rougeot et al., 1994), and the extracts and chromatographic fractions were analyzed for their capacity to inhibit the hydrolysis of the physiological substrate, substance P, by the human cell membranes containing NEP.

Extraction and purification of the human salivary compounds potentially regulators of enkephalinase activity. Briefly, following defrosted at +4° C., the saliva samples were treated according to the following procedure:

Methanol-acid extraction procedure: Extraction of low molecular-mass components in methanol-acid at 4° C.; to 1 volume of saliva was added 4 volumes of methanol containing 0.1% trifluoroacetic acid (TFA) solution. This first step realizes the elimination of proteins of high molecular weight (including the degrading enzymes), which are inactivated and precipitated in acid and methanol medium respectively and allows the solubilization of the salivary constituents of small molecular weight (≦10 Kda). The methanol mixture was quickly vortexed and centrifuged for 15 min at +4° C. and 12OOO g; the methanol was removed from the supernatant after lyophilization at −110° C.

HPLC cation-exchange chromatography (HPLC-EC): The methanol-extracted saliva was solubilized in the solvent A, i.e., ammonium acetate 10 mM pH 4.3, and injected into a HEMA-IEC BIO-1000 carboxymethyl column (Alltech). Components were eluted and isolated according to their cationic characteristic, in a two-step linear gradient of 10-500 mM and 500-900 mM ammonium acetate pH 4.7, respectively and at a 1 ml/min flow rate. Fractions of 2 ml were collected and tested after lyophilization for their inhibitory potency of the human ectopeptidase activity (LNCaP).

Quality and recovery of extraction and successive chromatographies were estimated using an internal standard (the tritiated peptide: 3H-YQRFSR) added to a representative salivary sample, as illustrated in FIG. 1; the recovery of the marker added to sample extracted corresponding to 2.5 ml of human saliva was evaluated at 75-84%. HPLC cation-exchange chromatography of methanol-extracted saliva (FIG. 2; representative profile of a salivary extract corresponding to 7 ml of human saliva) clearly revealed the presence of two major molecular salivary components, which were eluted within the first-step ammonium acetate gradient profile (10-500 mM) at retention times of 26-28 and 536-38 min respectively and that inhibited by ≧90% the endoproteolysis of substance P by human membrane-bound peptidases (The 2 active peaks visualized FIG. 2 with the retention times of 6 and 48 min correspond to the exclusion and total volume of the column, respectively).

Figure 3:
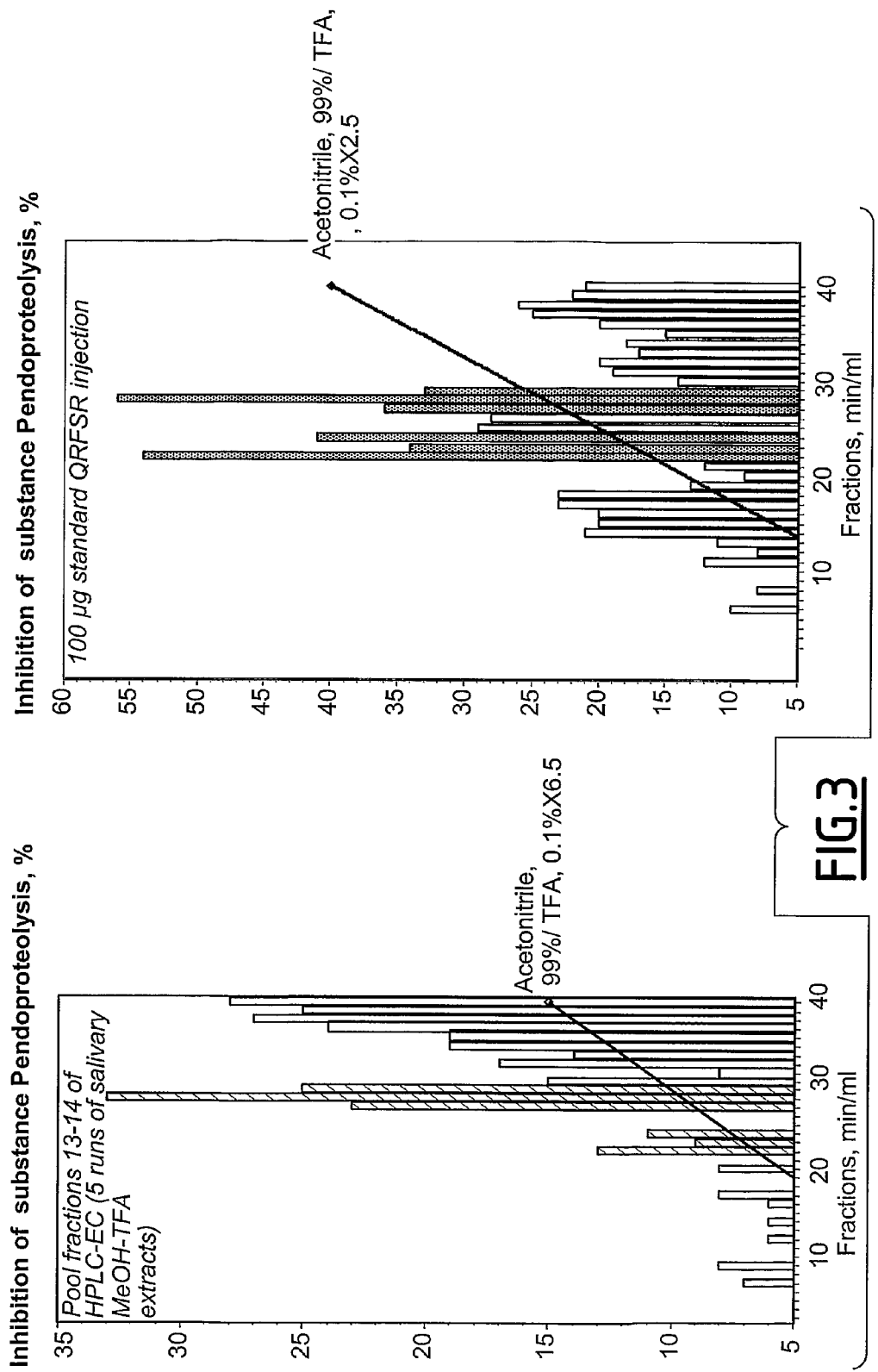
FIG. 3 is a representative reverse phase HPLC profile of the major HPLC-EC active 13-14 fractions (dotted bars). Fractions were analyzed for their inhibitory potency of substance P endoproteolysis by human ecto-endopeptidase activity (LNCaP cell line).

HPLC reverse-phase Chromatographies (RP-HPLC). The active fractions of the previous HPLC-EC were solubilized in the solvent A [0.1% TFA in H2O] and injected into a Synergi Max-RP column (Phenomenex). Sample components were eluted (1 ml/min) with a linear gradient of 1-99% solvent B [acetonitrile-TFA, 100-0.1, by vol.]. Fractions of 1 ml were collected and analyzed after lyophilization for their inhibitory potency towards the cell surface human ectopeptidase activity (LNCaP). The recovery of the internal marker was evaluated at 61%. Fractionation by RP-HPLC (FIG. 3), of the active molecular forms isolated from fractions 13-14 (26-28 min-retention time) of the previous HPLC-EC, showed the presence of two major molecular populations inhibiting the human endopeptidase activity, and that were eluted within the acetonitrile gradient profile at retention times of 23-25 and 28-30 min, respectively.

Figure 4:
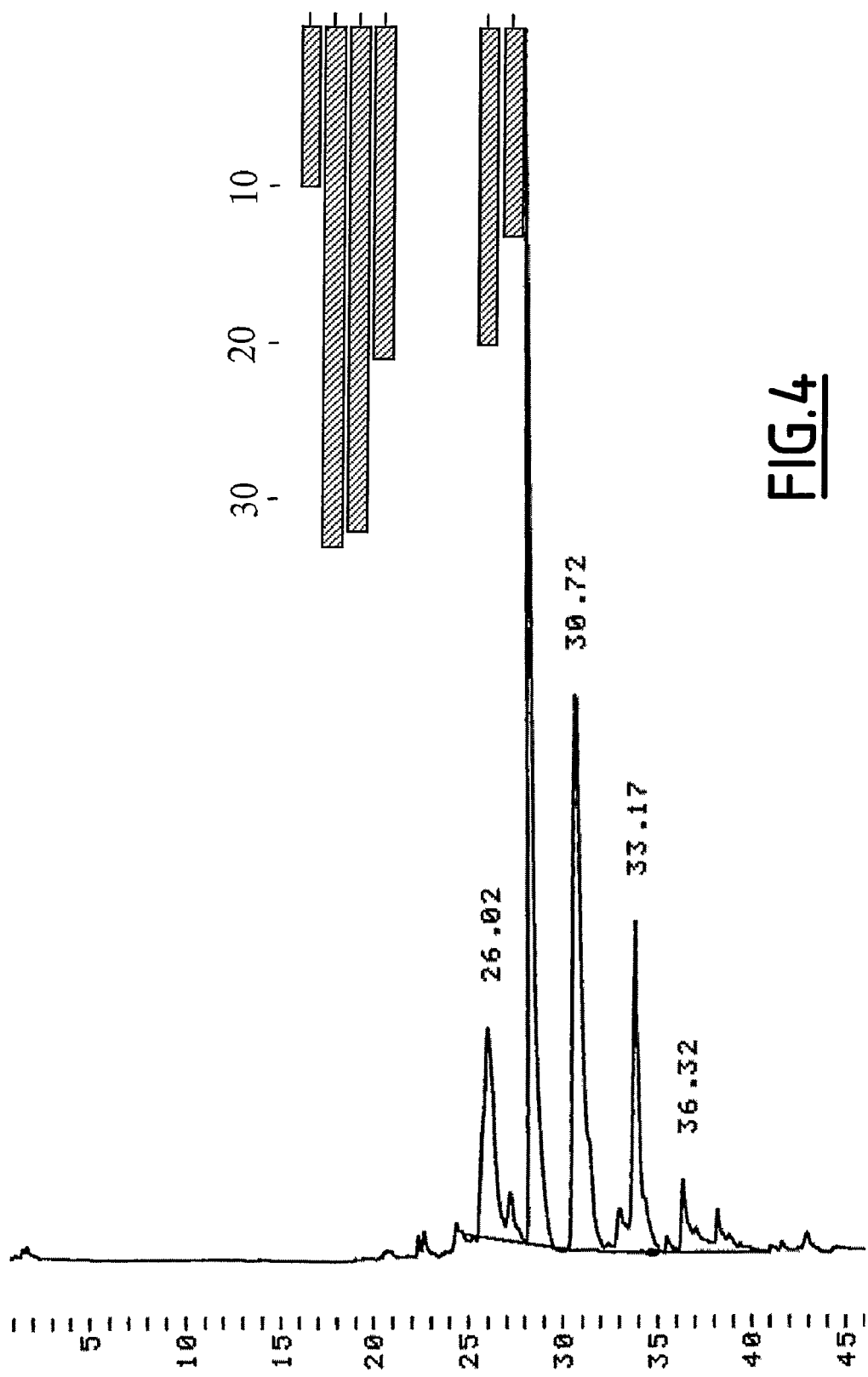
FIG. 4 is a representative reverse phase HPLC profile of the major HPLC-RP active fractions. Fractions were analyzed for their inhibitory potency of substance P endoproteolysis by human ecto-endopeptidase activity (black bars) and their absorbance at 274 nm (black line).

These fractions underwent further purification procedure on a new synergi Max-RP-HPLC column through elution with a linear gradient of 1-99% solvent B [100% methanol-0.1% TFA]. Column eluates were collected in microsorb tubes at 1-min intervals and the fractions were tested after lyophilisation for their NEP inhibitory activity. As shown in FIG. 4, two major molecular forms, which inhibited the endoproteolysis of substance P by human ectopeptidases, were thus isolated with retention times of 20-21 and 29-30 min respectively, and their amino acid sequences were determined.

Ciphergen ProteinChip and amino-acid sequence analyses. N-terminal sequence analysis was performed by automated Edman degradation using Applied Biosystems peptide sequanators (plate-forme d'Analyse et de Microséquençage des Protéines, Institut Pasteur). The molecular form eluting from the ultimate RP-HPLC at 18 min-retention time (fraction 20) corresponded to 690 and 769.5 Da molecular mass and to the following sequence of five amino acid residues: QRFSR (SEQ ID NO: 3). That one eluting at 26 min-retention time (fraction 28) corresponded to two molecular components of 622-666 Da and 6495 Da, respectively; the amino-acid determination of the highest molecular mass indicated that it corresponds to a salivary Basic Proline-Rich Polypeptide sequence, the human PRP-E of 61 amino-acid sequence (Isemura et al., 1982).

By analogy with the rat salivary sialorphin, these data provide direct evidence for the existence of a human salivary sialorphin-like, a QRFSR pentapeptide (SEQ ID NO: 3) of structure and function closely related to those of rat QHNPR pentapeptide (SEQ ID NO: 8) and which is secreted into the human salivary secretions; they support that QRFSR (SEQ ID NO: 3) is the mature product proteolytically processed from a precursor protein in a fashion similar to the maturation pathway of SMR1 and peptide-hormone precursors. Furthermore, as for the QHNPR rat peptide (SEQ ID NO: 8), the excreted QRFSR peptide (SEQ ID NO: 3) seems to be accumulated in the human salivary secretions under different forms, among which the free forms including probably an acetate salt form and the complex forms involving high hydrophobic interactions with salivary PRP-E.

Example 4

Synthesis and Testing of QRFSR (SEQ ID NO: 3) Peptide

Figure 6:
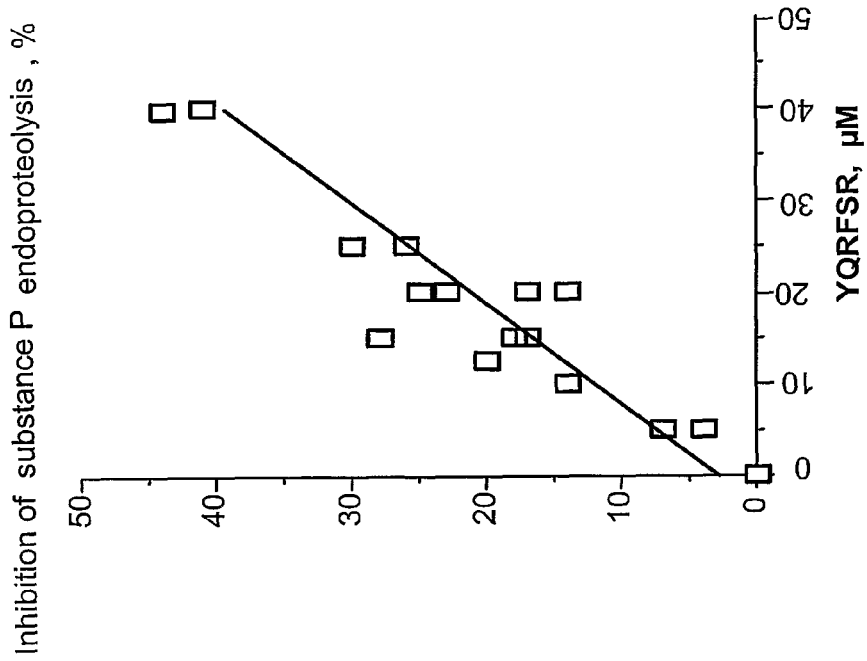
FIG. 6 shows the effect of YQRFSR (SEQ ID NO: 4) derivative of hBPLP-QRFSR peptide (SEQ ID NO: 3) on the breakdown of substance P by human ecto-endopeptidase activity (LNCaP cell line), the effective concentration of YQRFSR peptide (SEQ ID NO: 4) ranged from 5 to 50 µM and being half-maximal at 30 µM.
Figure 5:
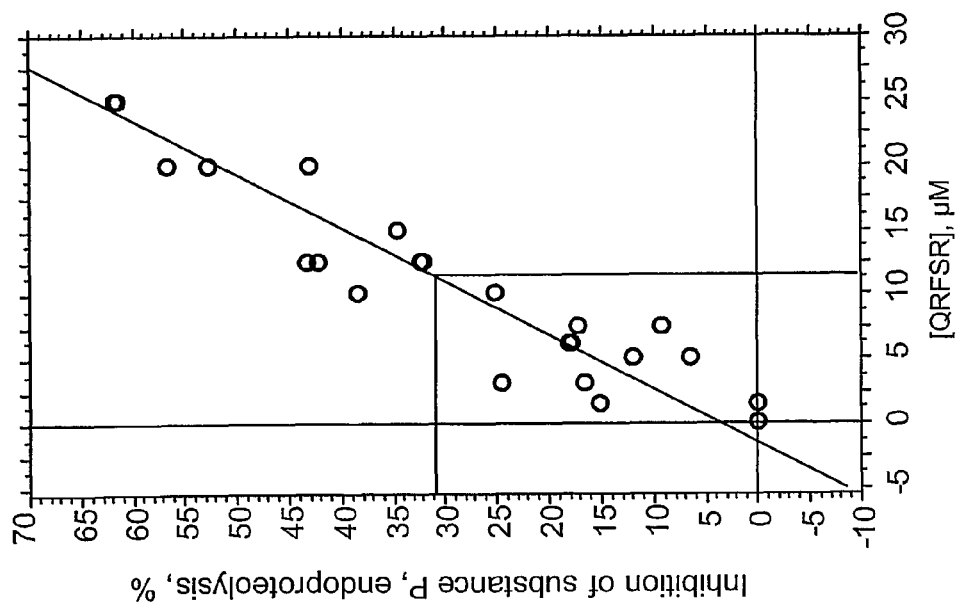
FIG. 5 shows the effect of BPLP-QRFSR peptide (SEQ ID NO: 3) on the breakdown of substance P by human ecto-endopeptidase activity (LNCaP cell line), the effective concentration of QRFSR peptide (SEQ ID NO: 3) ranged from 1 to 25 µM and being half-maximal at 11 µM.
Figure 7:
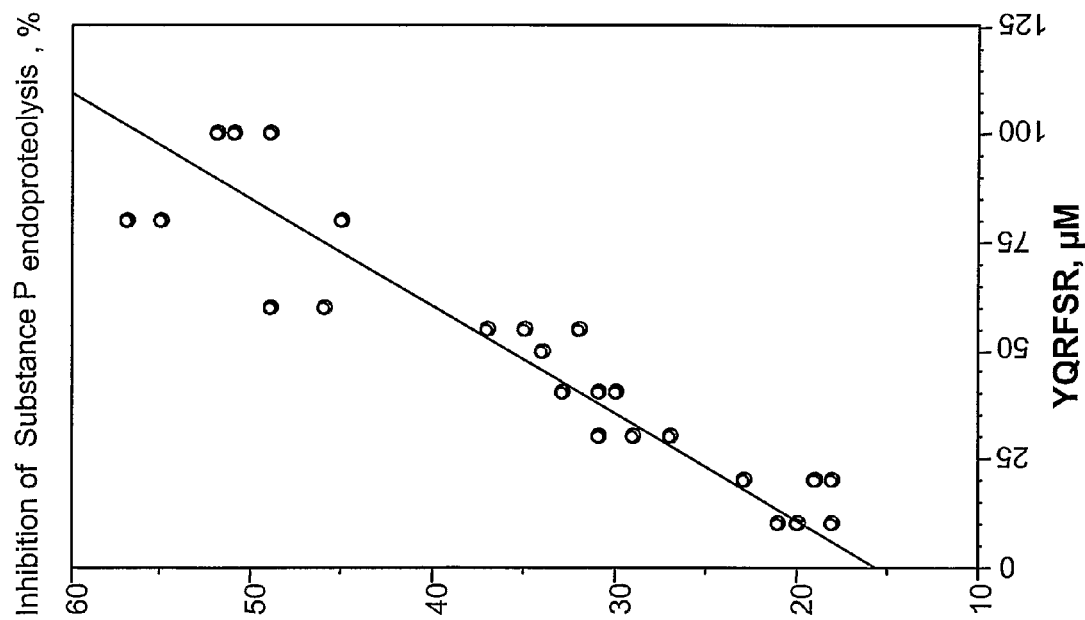
FIG. 7 shows the effect of YQRFSR (SEQ ID NO: 4) derivative of hBPLP-QRFSR peptide (SEQ ID NO: 3) on the breakdown of substance P by rat NEP ecto-endopeptidase activity (renal tissue), the effective concentration of YQRFSR peptide (SEQ ID NO: 4) ranged from 5 to 75 µM and being half-maximal at 38 µM.

The QRFSR peptide (SEQ ID NO: 3) was synthesized and analyzed for its capacity to inhibit the degradation of the physiological NEP substrate, the substance P, in vitro, in the experimental model of static incubation of human LNCaP cell membranes. The peptide QRFSR (SEQ ID NO: 3), inhibited the extra-cellular endoproteolysis of substance P mediated by human NEP expressed at the surface of human prostate epithelial cells. The effective concentration for QRFSR (SEQ ID NO: 3) ranged from 1 to 25 µM, and being half-maximal (IC50) at 11 µM (FIG. 5). Surprisingly, but in redundant way with regard to what was observed with rat sialorphin towards the human NEP, the inhibitory efficiency of the QRFSR human peptide (SEQ ID NO: 3) towards the rat renal NEP activity is at least 10-fold lower than that obtained towards the human cell surface NEP (LNCaP). Strikingly, the derivative peptide YQRFSR (SEQ ID NO: 4), which has been synthesized for tritium labeling and immunogenic conjugation for the development of antibody and immunoassay detection system, appeared to exhibit a relatively similar inhibitory efficacy towards both human and rat ecto-endopeptidase activities (FIGS. 6 and 7).

TABLE inhibitory potency of natural and derivative human and rat peptides towards both human and rat ectoendopeptidase activities:

| Ectoendopeptidase from | Human cells | Rat tissues |
| --- | --- | --- |
| QHNPR (SEQ ID NO: 8) | 4 to 40 µM | 0.4 to 4 µM |
| QHNP (SEQ ID NO: 9) | undetermined | $\geq$50 µM |
| QRFSR (SEQ ID NO: 3) | 2.5 to 25 µM | $\geq$100 µM |
| YQRFSR (SEQ ID NO: 4) | 5 to 50 µM | 5-75 µM |
| QRGPR (SEQ ID NO: 10) | $\geq$90 µM | undetermined |
| QRGPRGP (SEQ ID NO: 11) | $\geq$90 µM | undetermined |

Besides, the QRGPR peptide (SEQ ID NO: 10) (20-90 µM) which could be potentially maturated from hPB gene products, had no effect on substance P endoproteolysis induced by LNCaP human cell membranes; this result lets the inventors to propose that the nature of three central amino acids of the natural NEP-inhibitor pentapeptide (common Q-Nterminal and R-Cterminal) is determining signature for the affinity and/or specificity of their functional interaction with NEP ectoendopeptidase. Furthermore, in spite of the strong primary amino-acid sequence analogy between the rat and human NEP ($\neq$85%), the inventors observed a relative specificity in the functional interaction of both natural inhibitor-pentapeptides, respectively the rat QHNPR (SEQ ID NO: 8) and human QRFSR (SEQ ID NO: 3). All these results provide evidence for the existence of a conformational specificity in the secondary and tertiary of both ectoenzymes; the crystal structure determination of the binary complex formed with the sialorphin or its derivatives and the human NEP should allow to gain insight into the binding mode of these natural competitive inhibitors.

The inventors used the tritiated 3H-YQRFSR peptide (SEQ ID NO: 4) to establish the pharmacokinetic and pharmacodynamic parameters, of this human functional peptidomimetic of rat sialorphin in vivo in adult male rat (biodistribution-bioavailability-clearance) as well as to define its metabolism mechanism and turnover in vivo and in vitro, (FIG. 8). The RP-HPLC chromatographic characteristics revealed that:

the YQRFSR peptide (SEQ ID NO: 4) is not metabolized by human cell membranes containing NEP, indeed 93% was recovered as intact peptide against 94% in absence of metabolizing membranes, in the same experimental conditions, the YQRFSR peptide (SEQ ID NO: 4) inhibits by 70% the endoproteolysis of substance P by these human cell membranes.

Therefore, YQRFSR (SEQ ID NO: 4) is useful for investigating the analgesic activity of the BPLP maturation products in behavioral rat models of acute pain, e.g., the Pin pain test and Formalin test, which have been studied for the functional characterization of the sialorphin in vivo (Rougeot et al., 2003).

Example 5

Further Characterization of QRFSR (SEQ ID NO: 3) Peptides In Vitro

The inhibitory specificity of the QRFSR-peptide (SEQ ID NO: 3) was assessed by measuring the endoproteolysis of substance P (SP) in an in vitro enzyme-assay using purified soluble human NEP and human DPPIV (without the N-terminal cytosol and transmembrane segment). Using the selective recombinant hNEP assay, the molecular interaction of human QRFSR-peptide (SEQ ID NO: 3) with hNEP was established, providing direct evidence that the peptide inhibited hNEP activity: as shown on FIG. 9, QRFSR-peptide (SEQ ID NO: 3) prevented the NEP mediated-endoproteolysis of SP by 90%; its inhibitory potency was strictly concentration dependent ($r^2$=0.99, n=18), ranged from 5 to 50 µM and was half-maximal at 29±1 µM. In contrast, the breakdown of SP by recombinant hDPPIV was not prevented by 25 or 50 µM QRFSR-peptide (SEQ ID NO: 3), indicating that the inhibitory potency of the QRFSR-peptide (SEQ ID NO: 3) on the SP-catabolizing cell surface ectoenzymes in vitro, is simply due to its specific interaction with NEP-ectopeptidase. Furthermore, from studies monitoring the in vivo metabolism of SP, it appears likely that the QRFSR-peptide (SEQ ID NO: 3), like rat QHNPR-sialorphin (SEQ ID NO: 8), does not entirely protect endogenous SP from cleavage by the spinal SP-inactivating ectopeptidases, and therefore would not potentiate SP-mediated nociception in vivo.

The enkephalins are inactivated in vivo with remarkable efficiency (within a few seconds) by both ectopeptidases, NEP and APN. Owing to the complementary role of NEP and APN in enkephalin inactivation, only mixed NEP-APN synthetic inhibitors induce antinociceptive responses in various pain models.

Thus, the inhibitory specificity of QRFSR-peptide (SEQ ID NO: 3) was assessed in an enzyme-assay using membrane preparations of recombinant HEK human cells expressing selectively either human membrane-anchored NEP or APN. These transfected-cell models were developed in the laboratory. Membrane amino- and endo-ectopeptidase activities of human cell membranes were assayed in vitro by measuring the breakdown of artificial specific fluorogenic substrates, the NEP substrate used was: Mca-R-P-P-G-F-S-A-F-K-(Dnp)-OH (SEQ ID NO: 12) (Mca-BK2) and the APN substrate was: Ala-pNA. Using the selective membrane-anchored hNEP assay, the inventors found that the inhibition by the QRFSR-peptide (SEQ ID NO: 3) of Mca-BK2 endoproteolysis by NEP is concentration dependent ($r^2$=0.88, n=29 determination points) and the effective doses ranged from 5 to 50 µM. Using the selective membrane-anchored hAPN assay, the inventors have demonstrated that QRFSR-peptide (SEQ ID NO: 3) inhibits the Ala-pNA cleavage by hAPN at 10 to 90 µM effective doses ($r^2 \neq 0.93$, n=22 determination points) (see FIGS. 10 and 11).

TABLE 1

Summary of QRFSR (SEQ ID NO: 3) inhibitory effects ($IC_{50}$) on NEP and APN ectoenzyme activities, in vitro and ex vivo:

| Enzymes sources | Substrate | $IC_{50}$ values QRFSR-peptide |
|---|---|---|
| HEK-hNEP | Substance P (60 nM) | 14 µM |
|  | McaBK2 (5 µM) | 33 ± 6 µM |
| LNCaP | Substance P | 11 ± 3 µM |
|  | McaBK2 | 25 ± 1 µM |
| hNEP soluble | Substance P | 29 ± 1 µM |
| HEK-hAPN | Ala-pNA (100 µM) | 65 ± 9 µM |

These results indicate that the human QRFSR-pentapeptide (SEQ ID NO: 3) is an efficient dual inhibitor of NEP and APN ectopeptidase activities, in vitro. Furthermore, owing to the complementary role of NEP and APN in enkephalin inactivation and by analogy with rat sialorphin which exerts a powerful analgesic activity, the combined biological and genomic information accrued led the inventors to propose that the QRFSR-peptide (SEQ ID NO: 3), by inhibiting enkephalin-inactivating NEP-APN ectopeptidases, potentiates enkephalin-dependent antinociceptive mechanisms, in vivo.

Example 6

Functional Characterization of ORFSR (SEQ ID NO: 3) Peptide In Vivo

In spite of the strong primary amino-acid sequence analogy between the rat and human NEP (≠85%), the inventors observed a relative species-selectivity in the inhibitory potency of both inhibitor-pentapeptides, respectively the rat QHNPR (SEQ ID NO: 8) and human QRFSR (SEQ ID NO: 3). Strikingly, the derivative peptide YQRFSR (SEQ ID NO: 4), which was synthesized for tritium labeling, appeared to exhibit a relatively similar inhibitory efficacy towards both human and rat ectoendopeptidases (range of effective concentrations between 5 and 50 µM). Thus, the antinociceptive potency of the QRFSR-derived peptide (SEQ ID NO: 3) was investigated in the behavioral rat model of acute pain, i.e., the formalin test, which was used for the in vivo characterization of rat sialorphin action (Rougeot et al., 2003). Systemic administration of 0.5 and 1 mg/kg YQRFSR-peptide (SEQ ID NO: 4) inhibited the early phase (first 20 min after formalin injection) of paw licking of the formalin-injected hind paw. For instance, it significantly reduced the time spent by treated rats in paw licking from 144±17 s, n=8 (vehicle) to 97±14 s, n=8 (0.5 mg/kg) (p=0.05) and to 84±13 s, n=8 (1 mg/kg) (p=0.02 by Dunnett t-Test). Surprisingly, in contrast to rat sialorphin-treated rats, the YQRFSR peptide (SEQ ID NO: 4)-treated rats spent significantly less time in paw licking during the late phase (40 to 60 min after formalin injection) of the formalin test (vehicle-treated rats: 63±13 s vs. 1 mg/kg treated-rats: 9±3 s, p=0.001). Although less potent than rat sialorphin, in term of effective doses (100-200 µg/kg, iv), the QRFSR-derived peptide (SEQ ID NO: 3) seems to be as efficient in its pain-suppressive potency (1 mg/kg, iv), as the synthetic mixed NEP-APN inhibitor RB101 (2.5-5 mg/kg, iv) in the formalin-induced pain model.

These data (as presented on FIGS. 12, 13 and 14) clearly indicate that the YQRFSR-peptide (SEQ ID NO: 4) inhibits nociception induced by acute and long-acting chemical stimuli.

Its analgesic potency is almost as efficient as 3 mg/kg morphine dose.

Furthermore, the analgesia induced by the QRFSR-derived peptide (SEQ ID NO: 3) in the chemical-evoked pain behaviour is totally reversed in the presence of an opioid receptor antagonist, the nalaxone, which is consistent with an involvement of the endogenous opioidergic pathways in its analgesic effect.

REFERENCES

Beaumont et al, (1996) zinc metallopeptidases in health and disease, 105-129).

Dickinson, D. P., Thiesse, M., 1996. cDNA cloning of an abundant human lacrimal gland mRNA encoding a novel tear protein. Curr Eye Res. 15(4), 377-386.

Gante et al., Angew. Chem. Int. Ed. Engl. 33: 1699 (1994)

Gomeni R. et al., Computer-assisted drug development; an emerging technology for designing first-time-in-man and proof-of-concept studies from preclinical experiments. Eur. J. of Pharmaceutical Sciences (2001) 261-270

Horwell et al., Bioorg. Med. Chem. 4: 1573 (1996)

Isemura, S., Saitoh, E., 1997. Nucleotide sequence of gene PBI encoding a protein homologous to salivary proline-rich protein P-B. J Biochem (Tokyo). 121(6), 1025-1030.

Isemura, S., 2000. Nucleotide sequence of gene PBII encoding salivary proline-rich protein P-B. J Biochem (Tokyo). 127(3), 393-398.

Isemura, S., Saitoh, E., Sanada, K., 1982. Fractionation and characterization of basic proline-rich peptides of human parotid saliva and the amino acid sequence of proline-rich peptide P-E. J Biochem (Tokyo). 91(6), 2067-2075.

Jones E. et al., Drug discovery technology. Start-up shourcase and structure-based drug design. Drugs, September 2002; 5(9):894-895

Kan, impact of recombinant DNA technology and protein engineering on structure-based drug design: case studies of HIV-1 and HCMY proteases (2002).

Kenny et al, (1977) Proteinases in mammalian cells and tissues

Kenny et al, (1987) Mammalian ectoenzymes

Leissring et al., (2003) Enhanced Proteolysis of β-amyloid in APP transgenic mice prevents plaque formation, secondary pathology, and premature death, Neuron., 40, 1087-1093

Liskamp et al., Recl. Trav. Chim. Pays-Bas 1: 113 (1994)

Marini, M., Roda, L. G., 2000. Enkephalin-degrading enzymes and their inhibitors in human saliva. Peptides. 21(1), 125-135.

Newell et al., (2003) Thiorphan-induced neprilysin inhibition raises amyloid β levels in rabbit cortex and cerebrospinal fluid, Neuroscience letters 350, 178-180

Oefner C. et al. Structure of human Neutral Endopeptidase (Neprilysin) complexed with Phosphnomidon, J. Mol. Biol. (2000), 296, 341-349

Potempa J. and Travis. J., Proteinases as virulence factors in bacterial diseases and as potential targets for therapeutic interaction with proteinase inhibitors. In proteases as targets for therapy. 99, 159-188, Eds K. Helm, B. D. Korant and J. C. Cheronis-Spinger Handbook Exp. Pharm. 140.

Roques et al. (1993) Pharmacological Reviews 45, 87-146

Rosinski-Chupin, I., Tronik, D., Rougeon, F., 1988. High level of accumulation of a mRNA coding for a precursor-like protein in the submaxillary gland of male rats. Proc Natl Acad Sci USA. 85(22), 8553-8557.

Rougeot, C., Messaoudi, M., Hermitte, V., Rigault, A. G., Blisnick, T., Dugave, C., Desor, D., Rougeon, F., 2003. Sialorphin, a natural inhibitor of rat membrane-bound neutral endopeptidase that displays analgesic activity. Proc Natl Acad Sci USA. 100(14), 8549-8554.

Rougeot, C., Rosinski-Chupin, I., Njamkepo, E., Rougeon, F., 1994. Selective processing of submandibular rat 1 protein at dibasic cleavage sites. Salivary and bloodstream secretion products. Eur J. Biochem. 219(3), 765-773.

Rougeot, C., Vienet, R., Cardona, A., Le Doledec, L., Grognet, J. M.,

Rougeon, F., 1997. Targets for SMR1-pentapeptide suggest a link between the circulating peptide and mineral transport. Am J. Physiol. 273(4 Pt 2), R1309-1320.

Sambrook et al., (1989) *Molecular Cloning: A Laboratory Manual*, Second Edition Cold Spring Harbor Laboratory Press, Cold Spring Harbor, N.Y.

Seebach et al, Helv. Chim. Acta 79: 913 (1996)

Seidah et al., (1995) the mammalian family of subtilisin/Kexin-like, Pro-protein Convertases. Intramolecular chaperones and Protein folding; 9, 181-203

Turner et al. (2001) Bioessays, 23, 261-9

The invention claimed is:

1. An isolated peptide or a derivative thereof, wherein the peptide is derived from the human Basic Proline-rich Lacrimal Protein (BPLP) and:
   i) comprises the sequence X1-X2-Arg-Phe-Ser-Arg (SEQ ID NO:6), wherein: X1 represents H atom or a Tyr amino acid or a Cys amino acid; X2 represents Gln or Glp when X1 is H, or X2 represents Gln when XI is Tyr or Cys; and the sequence of SEQ ID NO:6 is the C-terminal part of said peptide,
   ii) consists of up to 15 amino acids, and
   iii) exhibits an inhibitory property against a neutral endopeptidase (NEP) or an aminopeptidase (APN);
   and wherein the derivative is obtained from said peptide by one to two amino acid substitutions, comprises the sequence of SEQ ID NO:6, and exhibits said inhibitory property against NEP or APN.

2. The peptide of claim 1, which exhibits the inhibitory property against NEP.

3. The peptide of claim 1, that consists of sequence X1-X2-Arg-Phe-Ser-Arg (SEQ ID NO: 6).

4. The peptide of claim 1, wherein the said peptide comprises the sequence QRFSR (SEQ ID NO: 3), YQRFSR (SEQ ID NO: 4), or CQRFSR (SEQ ID NO: 5).

5. The peptide of claim 4, which consists of sequence QRFSR (SEQ ID NO: 3).

6. The peptide of claim 4, which consists of sequence YQRFSR (SEQ ID NO: 4).

7. The peptide of claim 4, which consists of sequence CQRFSR (SEQ ID NO: 5).

8. A pharmaceutical composition comprising a peptide or a derivative thereof, wherein the peptide is derived from the human Basic Proline-rich Lacrimal Protein (BPLP) and:
   i) comprises the sequence X1-X2-Arg-Phe-Ser-Arg (SEQ ID NO:6), wherein: X1 represents H atom or a Tyr amino acid or a Cys amino acid; X2 represents Gln or Glp when X1 is H, or X2 represents Gln when XI is Tyr or Cys; and the sequence of SEQ ID NO:6 is the C-terminal part of said peptide,
   ii) consists of up to 15 amino acids, and
   iii) exhibits an inhibitory property against a neutral endopeptidase (NEP) or an aminopeptidase (APN);
   and wherein the derivative is obtained from said peptide by one to two amino acid substitutions, comprises the sequence of SEQ ID NO:6, and exhibits said inhibitory property against NEP or APN.

9. A pharmaceutical composition comprising a polymer of a peptide or a derivative thereof, wherein the peptide is derived from the human Basic Proline-rich Lacrimal Protein (BPLP) and:
   i) comprises the sequence X1-X2-Arg-Phe-Ser-Arg (SEQ ID NO:6), wherein: X1 represents H atom or a Tyr amino acid or a Cys amino acid; X2 represents Gln or Glp when X1 is H, or X2 represents Gln when XI is Tyr or Cys; and the sequence of SEQ ID NO:6 is the C-terminal part of said peptide,
   ii) consists of up to 15 amino acids, and
   iii) exhibits an inhibitory property against a neutral endopeptidase (NEP) or an aminopeptidase (APN);
   and wherein the derivative is obtained from said peptide by one to two amino acid substitutions, comprises the sequence of SEQ ID NO:6, and exhibits said inhibitory property against NEP or APN.

* * * * *

SEQUENCE LISTING

```
<160> NUMBER OF SEQ ID NOS: 15

<210> SEQ ID NO 1
<211> LENGTH: 947
<212> TYPE: DNA
<213> ORGANISM: Homo sapiens
<220> FEATURE:
<221> NAME/KEY: CDS
<222> LOCATION: (81)..(686)

<400> SEQUENCE: 1
aattgagtat ctggcaagag taagattaag cagtaatttg ttccaaagaa gaatcttcta      60
ccaaggagca actttaaaga atg aaa tta act ttc ttc ttg ggc ctg ttg gct    113
                      Met Lys Leu Thr Phe Phe Leu Gly Leu Leu Ala
                        1               5                      10 ctt att tca tgt ttc aca ccc agt gag agt caa aga ttc tcc aga aga      161
Leu Ile Ser Cys Phe Thr Pro Ser Glu Ser Gln Arg Phe Ser Arg Arg
             15                  20                  25 cca tat cta cct ggc cag ctg cca cca cct cca ctc tac agg cca aga      209
Pro Tyr Leu Pro Gly Gln Leu Pro Pro Pro Pro Leu Tyr Arg Pro Arg
         30                  35                  40 tgg gtt cca cca agt ccc cca cct ccc tat gac tca aga ctt aat tca      257
Trp Val Pro Pro Ser Pro Pro Pro Pro Tyr Asp Ser Arg Leu Asn Ser
     45                  50                  55 cca ctt tct ctt ccc ttt gtc cca ggg cga gtt cca cca tct tct ttc      305
Pro Leu Ser Leu Pro Phe Val Pro Gly Arg Val Pro Pro Ser Ser Phe
 60                  65                  70                  75 tct cga ttt agc caa gca gtc att cta tct caa ctc ttt cca ttg gaa      353
Ser Arg Phe Ser Gln Ala Val Ile Leu Ser Gln Leu Phe Pro Leu Glu
                 80                  85                  90 tct att aga caa cct cga ctc ttt ccg ggt tat cca aac cta cat ttc      401
Ser Ile Arg Gln Pro Arg Leu Phe Pro Gly Tyr Pro Asn Leu His Phe
             95                 100                 105 cca cta aga cct tac tat gta gga cct att agg ata tta aaa ccc cca      449
Pro Leu Arg Pro Tyr Tyr Val Gly Pro Ile Arg Ile Leu Lys Pro Pro
        110                 115                 120 ttt cct cct att cct ttt ttt ctt gct att tac ctt cct atc tct aac      497
Phe Pro Pro Ile Pro Phe Phe Leu Ala Ile Tyr Leu Pro Ile Ser Asn
    125                 130                 135 cct gag ccc caa ata aac atc acc acc gca gat aca aca atc acc aca      545
Pro Glu Pro Gln Ile Asn Ile Thr Thr Ala Asp Thr Thr Ile Thr Thr
140                 145                 150                 155
```

```
aat ccc ccc acc act gca aca gca acc acc agg cac ttc cac aaa acc     593
Asn Pro Pro Thr Thr Ala Thr Ala Thr Thr Arg His Phe His Lys Thr
            160                 165                 170 cac aat gac gat cag ctc ctc aac agt acc tat ctc ttc aac acc aga     641
His Asn Asp Asp Gln Leu Leu Asn Ser Thr Tyr Leu Phe Asn Thr Arg
            175                 180                 185 gcc tgc cac ctc cat atc agc agc aac ccc cgc agc atc tac tga         686
Ala Cys His Leu His Ile Ser Ser Asn Pro Arg Ser Ile Tyr
            190                 195                 200 aaatactact caaattctcg ccaaccgtcc tcacacagta ttgctcaatg ccactgtcca    746
agttacgact tccaaccaaa ctatattaag cagcccagcc tttaaaagtt tttggcaaaa    806
actctttgcc attttggtt gaacatgcaa taaatgatat tttccaaact gctctgatat     866
cttagaagaa ataaactgca atgatttga tggaaccaac cctgatctaa ccagcacact     926
aaataaagta tttgagcaat a                                             947

<210> SEQ ID NO 2
<211> LENGTH: 201
<212> TYPE: PRT
<213> ORGANISM: Homo sapiens

<400> SEQUENCE: 2

Met Lys Leu Thr Phe Phe Leu Gly Leu Leu Ala Leu Ile Ser Cys Phe
1               5                   10                  15

Thr Pro Ser Glu Ser Gln Arg Phe Ser Arg Arg Pro Tyr Leu Pro Gly
            20                  25                  30

Gln Leu Pro Pro Pro Leu Tyr Arg Pro Arg Trp Val Pro Ser
        35                  40                  45

Pro Pro Pro Pro Tyr Asp Ser Arg Leu Asn Ser Pro Leu Ser Leu Pro
    50                  55                  60

Phe Val Pro Gly Arg Val Pro Pro Ser Ser Arg Phe Ser Gln
65                  70                  75                  80

Ala Val Ile Leu Ser Gln Leu Phe Pro Leu Glu Ser Ile Arg Gln Pro
                85                  90                  95

Arg Leu Phe Pro Gly Tyr Pro Asn Leu His Phe Pro Leu Arg Pro Tyr
            100                 105                 110

Tyr Val Gly Pro Ile Arg Ile Leu Lys Pro Pro Phe Pro Ile Pro
        115                 120                 125

Phe Phe Leu Ala Ile Tyr Leu Pro Ile Ser Asn Pro Glu Pro Gln Ile
    130                 135                 140

Asn Ile Thr Thr Ala Asp Thr Thr Ile Thr Thr Asn Pro Pro Thr Thr
145                 150                 155                 160

Ala Thr Ala Thr Thr Arg His Phe His Lys Thr His Asn Asp Asp Gln
                165                 170                 175

Leu Leu Asn Ser Thr Tyr Leu Phe Asn Thr Arg Ala Cys His Leu His
            180                 185                 190

Ile Ser Ser Asn Pro Arg Ser Ile Tyr
        195                 200

<210> SEQ ID NO 3
<211> LENGTH: 5
<212> TYPE: PRT
<213> ORGANISM: Homo sapiens

<400> SEQUENCE: 3

Gln Arg Phe Ser Arg
1               5
```

```
<210> SEQ ID NO 4
<211> LENGTH: 6
<212> TYPE: PRT
<213> ORGANISM: Homo sapiens

<400> SEQUENCE: 4

Tyr Gln Arg Phe Ser Arg
1               5

<210> SEQ ID NO 5
<211> LENGTH: 6
<212> TYPE: PRT
<213> ORGANISM: Homo sapiens

<400> SEQUENCE: 5

Cys Gln Arg Phe Ser Arg
1               5

<210> SEQ ID NO 6
<211> LENGTH: 6
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Xaa2 is Gln or Glp when Xaa1 is not present.
      Xaa2 is Gln when Xaa1 is Tyr or Cys.

<400> SEQUENCE: 6

Xaa Xaa Arg Phe Ser Arg
1               5

<210> SEQ ID NO 7
<211> LENGTH: 5
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa1 is Glp.

<400> SEQUENCE: 7

Xaa Arg Phe Ser Arg
1               5

<210> SEQ ID NO 8
<211> LENGTH: 5
<212> TYPE: PRT
<213> ORGANISM: Rattus rattus

<400> SEQUENCE: 8

Gln His Asn Pro Arg
1               5

<210> SEQ ID NO 9
<211> LENGTH: 4
<212> TYPE: PRT
<213> ORGANISM: Rattus rattus

<400> SEQUENCE: 9

Gln His Asn Pro
1

<210> SEQ ID NO 10
<211> LENGTH: 5
<212> TYPE: PRT
<213> ORGANISM: Homo sapiens
```

```
<400> SEQUENCE: 10

Gln Arg Gly Pro Arg
1               5

<210> SEQ ID NO 11
<211> LENGTH: 7
<212> TYPE: PRT
<213> ORGANISM: Homo sapiens

<400> SEQUENCE: 11

Gln Arg Gly Pro Arg Gly Pro
1               5

<210> SEQ ID NO 12
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Arg at position 1 is modified with
      (7-methoxycoumarin-4-yl)acetyl
<220> FEATURE:
<221> NAME/KEY: MISC_FEATURE
<222> LOCATION: (10)..(10)
<223> OTHER INFORMATION: hydroxy substituted 2,4-dinitrophenyl amino
      acid

<400> SEQUENCE: 12

Arg Pro Pro Gly Phe Ser Ala Phe Lys Xaa
1               5                   10

<210> SEQ ID NO 13
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Ala at position 1 is modified with succinyl
<220> FEATURE:
<221> NAME/KEY: MISC_FEATURE
<222> LOCATION: (3)..(3)
<223> OTHER INFORMATION: Phe at position 3 is modified with 7-amino-4-
      methyl coumarin

<400> SEQUENCE: 13

Ala Ala Phe
1

<210> SEQ ID NO 14
<211> LENGTH: 11
<212> TYPE: PRT
<213> ORGANISM: Homo sapiens

<400> SEQUENCE: 14

Arg Phe Lys Phe Gln Gln Phe Phe Gly Leu Met
1               5                   10

<210> SEQ ID NO 15
<211> LENGTH: 5
```

```
<212> TYPE: PRT
<213> ORGANISM: Homo sapiens

<400> SEQUENCE: 15

Tyr Gly Gly Phe Met
1               5
```